US011112407B2

(12) United States Patent
Komorowski et al.

(10) Patent No.: US 11,112,407 B2
(45) Date of Patent: Sep. 7, 2021

(54) DIAGNOSIS OF A NEUROLOGICAL DISEASE

(71) Applicant: EUROIMMUN Medizinische Labordiagnostika AG, Lübeck (DE)

(72) Inventors: Lars Komorowski, Ratzeburg (DE); Madeleine Scharf, Lübeck (DE); Ramona Miske, Lübeck (DE); Yvonne Denno, Lübeck (DE); Inga-Madeleine Dettmann, Ahrensbök (DE); Christian Probst, Ratzeburg (DE); Fedor Heidenreich, Hannover (DE); Ralf Gieß, Hannover (DE)

(73) Assignee: EUROIMMUN Medizinische Labordiagnostika AG, Lübeck (DE)

( * ) Notice: Subject to any disclaimer, the term of this patent is extended or adjusted under 35 U.S.C. 154(b) by 0 days.

(21) Appl. No.: 14/729,609

(22) Filed: Jun. 3, 2015

(65) Prior Publication Data

US 2015/0355177 A1 Dec. 10, 2015

(30) Foreign Application Priority Data

Jun. 6, 2014 (EP) .................................... 14171561

(51) Int. Cl.

| | |
|---|---|
| ***G01N 33/564*** | (2006.01) |
| ***G01N 33/68*** | (2006.01) |
| ***C07K 16/06*** | (2006.01) |
| ***A61K 39/00*** | (2006.01) |
| ***C12N 9/14*** | (2006.01) |
| ***C07K 16/40*** | (2006.01) |
| ***A61K 38/47*** | (2006.01) |

(52) U.S. Cl.

CPC .......... *G01N 33/564* (2013.01); *A61K 38/47* (2013.01); *C07K 16/06* (2013.01); *C07K 16/40* (2013.01); *C12N 9/14* (2013.01); *G01N 33/6896* (2013.01); *A61K 2039/505* (2013.01); *C07K 2317/73* (2013.01); *C12Y 306/03009* (2013.01); *G01N 2333/914* (2013.01); *G01N 2800/28* (2013.01)

(58) Field of Classification Search

CPC ............... G01N 33/564; G01N 33/574; G01N 2800/2835; G01N 33/6896; G01N 2800/28; G01N 2333/914; C07K 16/06; C07K 16/40; C07K 2317/73; C12N 9/14; C12Y 306/03009; A61P 35/00; A61P 25/14; A61P 25/00; A61K 38/00; A61K 38/47; A61K 2039/505

See application file for complete search history.

(56) References Cited

FOREIGN PATENT DOCUMENTS

| | | | |
|---|---|---|---|
| EP | 2 605 017 A1 | | 6/2013 |
| WO | WO2005108415 | * | 11/2005 |
| WO | 2008/055530 A1 | | 5/2008 |
| WO | WO/2008/054792 | * | 5/2008 |
| WO | 2010/070043 A1 | | 6/2010 |

OTHER PUBLICATIONS

Aguiar et al., Neuron, 43:169-175, Jul. 22, 2004.*
Baba et al., J Am College Cardiology, vol. 40, No. 6:1153-1159, 2002.*
H00000478-Q01 datasheet published by Novusbio.com, cataloged Nov. 6, 2009. Retrieved online from <http://www.novusbio.com/productsearch?keys=Sodium+Potassium+ATPase+Alpha+3> Retrieved on Sep. 9, 2016.*
NBL1-07809 datasheet published by Novusbio.com, cataloged Nov. 6, 2009. Retrieved online from <http://www.novusbio.com/productsearch?keys=Sodium+Potassium+ATPase+Alpha+3> Retrieved on Sep. 9, 2016.*
Fritzler et al., Arthritis Research and Therapy, 5(4):192-201, Jun. 2003.*
Sigma-Aldrich M5785 product sheet, published Apr. 27, 2012 [online]. Retrieved from: <http://web.archive.org/web/20120427192414/http://www.sigmaaldrich.com/catalog/product/sigma/m5785?lang=en®ion=> Retrieved on: Jan. 30, 2017 7:55:22 PM.*
Towle et al., J Experimental Biol., 204:4005-4012, 2001 (Year: 2001).*
Jarius et al., J Neuroinflammation, vol. 11, Article No. 46, Mar. 8, (Year: 2014).*
Benfante et al., Biochem. J. 386:63-72, (Year: 2005).*
Ricciuti et al., J Clin Endocrinol Metab., 99(5):1758-66, May (Year: 2014).*
Miyaji et al., Proteomics 2:1489-93, (Year: 2002).*
Extended European Search Report dated Sep. 12, 2014 for corresponding EP Application No. 14171561.5-1408, 7 pages.
Gáti et al., "Sensory ataxic neuropathy with dysarthria/dysphagia and opthalmoplegia (SANDO). Two case reports," *Acta Myologica XXX*:188-190, 2011.
Rosewich et al., "The expanding clinical and genetic spectrum of ATP1A3-related disorders," *Neurology 82*:945-955, Feb. 12, 2004.
The UniProt Consortium, "Na+/K+ transporting alpha 3 polypeptide," UniProt Knowledgebase, retrieved from http://www.uniprot.org/uniprot/D2WKD7, on Sep. 11, 2015, 7 pages.
(Continued)

*Primary Examiner* — Kimberly Ballard
*Assistant Examiner* — Stacey N MacFarlane
(74) *Attorney, Agent, or Firm* — Seed IP Law Group LLP

(57) ABSTRACT

The present invention relates to a method for diagnosing a disease, comprising the step detecting in a sample an autoantibody binding to the alpha 3 subunit of the human neuronal Na(+)/K(+) ATPase, an isolated and/or recombinant polypeptide comprising the alpha 3 subunit of the human neuronal Na(+)/K(+) ATPase, a use of a membrane-associated human Na(+)/K(+) ATPase or a variant thereof for the diagnosis of a disease, an isolated and/or recombinant polypeptide comprising the alpha 3 subunit of the human neuronal Na(+)/K(+) ATPase or a variant thereof, for use in the treatment of a disease, an autoantibody binding to said polypeptide and a method for isolating such autoantibody, a pharmaceutical composition, medical or diagnostic device or test kit comprising the polypeptide.

6 Claims, 6 Drawing Sheets

Specification includes a Sequence Listing.

(56) References Cited

OTHER PUBLICATIONS

The UniProt Consortium, "Sodium/potassium-transporting ATPase subunit alpha-3," UniProt Knowledgebase, retrieved from http://www.uniprot.org/uniprot/P06687, on Sep. 11, 2015, 14 pages.
The UniProt Consortium, "Sodium/potassium-transporting ATPase subunit beta-1," UniProt Knowledgebase, retrieved from http://www.uniprot.org/uniprot/P07340, on Sep. 11, 2015, 11 pages.
The UniProt Consortium, "Sodium/potassium-transporting ATPase subunit alpha-3," UniProt Knowledgebase, retrieved from http://www.uniprot.org/uniprot/P13637, on Sep. 11, 2015, 26 pages.
Office Action for European Application No. 14 171 561.5-1408, (6 pages) dated Aug. 2, 2017.
Scharf et al., "Neuronal $Na^+/K^+$ ATPase is an autoantibody target in paraneoplastic neurologic syndrome," *Neurology 84*:1673-1679 (2015).
Office Action for European Application No. 14 171 561.5-1408, (10 pages) dated Jul. 4, 2016.

* cited by examiner

SEQUENCE LISTING

```
<160> NUMBER OF SEQ ID NOS: 15

<210> SEQ ID NO 1
<211> LENGTH: 9
<212> TYPE: PRT
<213> ORGANISM: Artificial sequence
<220> FEATURE:
<223> OTHER INFORMATION: Peptide sequence of either rattus norvegicus
      or sus scrofa

<400> SEQUENCE: 1

Leu Ile Ile Val Glu Gly Cys Gln Arg
1               5


<210> SEQ ID NO 2
<211> LENGTH: 11
<212> TYPE: PRT
<213> ORGANISM: Artificial sequence
<220> FEATURE:
<223> OTHER INFORMATION: Peptide sequence of either rattus norvegicus
      or sus scrofa

<400> SEQUENCE: 2

Leu Asn Ile Pro Val Ser Gln Val Asn Pro Arg
1               5                   10


<210> SEQ ID NO 3
<211> LENGTH: 11
<212> TYPE: PRT
<213> ORGANISM: Rattus norvegicus

<400> SEQUENCE: 3

Thr Glu Ile Ser Phe Arg Pro Asn Asp Pro Lys
1               5                   10


<210> SEQ ID NO 4
<211> LENGTH: 11
<212> TYPE: PRT
```

-continued

<213> ORGANISM: Rattus norvegicus

<400> SEQUENCE: 4

Ser Tyr Glu Ala Tyr Val Leu Asn Ile Ile Arg
1 5 10

<210> SEQ ID NO 5
<211> LENGTH: 8684
<212> TYPE: DNA
<213> ORGANISM: artificial
<220> FEATURE:
<223> OTHER INFORMATION: vector comprising sequence encoding human ATPase

<400> SEQUENCE: 5
aggccaccat gggggacaag aaagatgaca aggactcacc caagaagaac aagggcaagg 60
agcgccggga cctggatgac ctcaagaagg aggtggctat gacagagcac aagatgtcag 120
tggaagaggt ctgccggaaa tacaacacag actgtgtgca gggtttgacc cacagcaaag 180
cccaggagat cctggcccgg gatgggccta acgcactcac gccaccgcct accaccccag 240
agtgggtcaa gttttgccgg cagctcttcg gggcttctc catcctgctg tggatcgggg 300
ctatcctctg cttcctggcc tacggtatcc aggcgggcac cgaggacgac ccctctggtg 360
acaacctgta cctgggcatc gtgctggcgg ccgtggtgat catcactggc tgcttctcct 420
actaccagga ggccaagagc tccaagatca tggagtcctt caagaacatg gtgccccagc 480
aagccctggt gatccgggaa ggtgagaaga tgcaggtgaa cgctgaggag gtggtggtcg 540
gggacctggt ggagatcaag ggtggagacc gagtgccagc tgacctgcgg atcatctcag 600
cccacggctg caaggtggac aactcctccc tgactggcga atccgagccc cagactcgct 660
ctcccgactg cacgcacgac aaccccttgg agactcggaa catcaccttc ttttccacca 720
actgtgtgga aggcacggct cggggcgtgg tggtggccac gggcgaccgc actgtcatgg 780
gccgtatcgc caccctggca tcagggctgg aggtgggcaa gacgcccatc gccatcgaga 840
ttgagcactt catccagctc atcaccggcg tggctgtctt cctgggtgtc tccttcttca 900
tcctctccct cattctcgga tacacctggc ttgaggctgt catcttcctc atcggcatca 960
tcgtggccaa tgtcccagag ggtctgctgg ccactgtcac tgtgtgtctg acgctgaccg 1020
ccaagcgcat ggcccggaag aactgcctgg tgaagaacct ggaggctgta gaaaccctgg 1080
gctccacgtc caccatctgc tcagataaga cagggaccct cactcagaac cgcatgacag 1140
tcgcccacat gtggtttgac aaccagatcc acgaggctga caccactgag gaccagtcag 1200
ggacctcatt tgacaagagt tcgcacacct gggtggccct gtctcacatc gctgggctct 1260
gcaatcgcgc tgtcttcaag ggtggtcagg acaacatccc tgtgctcaag agggatgtgg 1320
ctggggatgc gtctgagtct gccctgctca agtgcatcga gctgtcctct ggctccgtga 1380
agctgatgcg tgaacgcaac aagaaagtgg ctgagattcc cttcaattcc accaacaaat 1440
accagctctc catccatgag accgaggacc ccaacgacaa ccgatacctg ctggtgatga 1500
agggtgcccc cgagcgcatc ctggaccgct gctccaccat cctgctacag ggcaaggagc 1560
agcctctgga cgaggaaatg aaggaggcct tccagaatgc ctaccttgag ctcggtggcc 1620
tgggcgagcg cgtgcttggt ttctgccatt attacctgcc cgaggagcag ttccccaagg 1680
gctttgcctt cgactgtgat gacgtgaact tcaccacgga caacctctgc tttgtgggcc 1740
tcatgtccat gatcgaccca ccccgggcag ccgtccctga cgcggtgggc aagtgtcgca 1800
gcgcaggcat caaggtcatc atggtcaccg gcgatcaccc catcacggcc aaggccattg 1860

-continued

```
ccaagggtgt gggcatcatc tctgagggca acgagactgt ggaggacatc gccgcccggc   1920
tcaacattcc cgtcagccag gttaaccccc gggatgccaa ggcctgcgtg atccacggca   1980
ccgacctcaa ggacttcacc tccgagcaaa tcgacgagat cctgcagaat cacaccgaga   2040
tcgtcttcgc ccgcacatcc ccccagcaga agctcatcat tgtggagggc tgtcagagac   2100
agggtgcaat tgtggctgtg accggggatg gtgtgaacga ctcccccgct ctgaagaagg   2160
ccgacattgg ggtggccatg ggcatcgctg gctctgacgt ctccaagcag gcagctgaca   2220
tgatcctgct ggacgacaac tttgcctcca tcgtcacagg ggtggaggag ggccgcctga   2280
tcttcgacaa cctaaagaag tccattgcct acaccctgac cagcaatatc ccggagatca   2340
cgcccttcct gctgttcatc atggccaaca tcccgctgcc cctgggcacc atcaccatcc   2400
tctgcatcga tctgggcact gacatggtcc ctgccatctc actggcgtac gaggctgccg   2460
aaagcgacat catgaagaga cagcccagga acccgcggac ggacaaattg gtcaatgaga   2520
gactcatcag catggcctac gggcagattg gaatgatcca ggctctcggt ggcttcttct   2580
cttactttgt gatcctggca gaaaatggct tcttgcccgg caacctggtg ggcatccggc   2640
tgaactggga tgaccgcacc gtcaatgacc tggaagacag ttacgggcag cagtggacat   2700
acgagcagag gaaggtggtg gagttcacct gccacacggc cttctttgtg agcatcgttg   2760
tcgtccagtg ggccgatctg atcatctgca agacccggag gaactcggtc ttccagcagg   2820
gcatgaagaa caagatcctg atcttcgggc tgtttgagga gacggccctg gctgccttcc   2880
tgtcctactg ccccggcatg gacgtggccc tgcgcatgta ccctctcaag cccagctggt   2940
ggttctgtgc cttcccctac agtttcctca tcttcgtcta cgacgaaatc cgcaaactca   3000
tcctgcgcag gaacccaggg ggttgggtgg agaaggaaac ctactactag gcctcatggg   3060
ccggcgcgcc caccaccacc accaccactg acactaagtg attaacctca ggtgcaggct   3120
gcctatcaga aggtggtggc tggtgtggcc aatgccctgg ctcacaaata ccactgagat   3180
cgatcttttt ccctctgcca aaaattatgg ggacatcatg aagccccttg agcatctgac   3240
ttctggctaa taaaggaaat ttattttcat tgcaatagtg tgttggaatt ttttgtgtct   3300
ctcactcgga aggacatatg ggagggcaaa tcatttaaaa catcagaatg agtatttggt   3360
ttagagtttg gcaacatatg cccatatgta actagcataa ccccttgggg cctctaaacg   3420
ggtcttgagg ggtttttttgc tgaaagcatg cggaggaaat tctccttgaa gtttccctgg   3480
tgttcaaagt aaaggagttt gcaccagacg cacctctgtt cactggtccg gcgtattaaa   3540
acacgataca ttgttattag tacatttatt aagcgctaga ttctgtgcgt tgttgattta   3600
cagacaattg ttgtacgtat tttaataatt cattaaattt ataatcttta gggtggtatg   3660
ttagagcgaa aatcaaatga ttttcagcgt ctttatatct gaatttaaat attaaatcct   3720
caatagattt gtaaaatagg tttcgattag tttcaaacaa gggttgtttt tccgaaccga   3780
tggctggact atctaatgga ttttcgctca acgccacaaa acttgccaaa tcttgtagca   3840
gcaatctagc tttgtcgata ttcgtttgtg ttttgttttg taataaaggt tcgacgtcgt   3900
tcaaaatatt atgcgctttt gtatttcttt catcactgtc gttagtgtac aattgactcg   3960
acgtaaacac gttaaataga gcttggacat atttaacatc gggcgtgtta gctttattag   4020
gccgattatc gtcgtcgtcc caaccctcgt cgttagaagt tgcttccgaa gacgattttg   4080
ccatagccac acgacgccta ttaattgtgt cggctaacac gtccgcgatc aaatttgtag   4140
ttgagctttt tggaattatt tctgattgcg ggcgtttttg ggcgggtttc aatctaactg   4200
```

-continued

```
tgcccgattt taattcagac aacacgttag aaagcgatgg tgcaggcggt ggtaacattt   4260
cagacggcaa atctactaat ggcggcggtg gtggagctga tgataaatct accatcggtg   4320
gaggcgcagg cggggctggc ggcggaggcg gaggcggagg tggtggcggt gatgcagacg   4380
gcggtttagg ctcaaatgtc tctttaggca acacagtcgg cacctcaact attgtactgg   4440
tttcgggcgc cgtttttggt ttgaccggtc tgagacgagt gcgatttttt tcgtttctaa   4500
tagcttccaa caattgttgt ctgtcgtcta aaggtgcagc gggttgaggt tccgtcggca   4560
ttggtggagc gggcggcaat tcagacatcg atggtggtgg tggtggtgga ggcgctggaa   4620
tgttaggcac gggagaaggt ggtggcggcg gtgccgccgg tataatttgt tctggtttag   4680
tttgttcgcg cacgattgtg ggcaccggcg caggcgccgc tggctgcaca acggaaggtc   4740
gtctgcttcg aggcagcgct tggggtggtg gcaattcaat attataattg gaatacaaat   4800
cgtaaaaatc tgctataagc attgtaattt cgctatcgtt taccgtgccg atatttaaca   4860
accgctcaat gtaagcaatt gtattgtaaa gagattgtct caagctcgga acgctgcgct   4920
cggtcgttcg gctgcggcga gcggtatcag ctcactcaaa ggcggtaata cggttatcca   4980
cagaatcagg ggataacgca ggaaagaaca tgtgagcaaa aggccagcaa aaggccagga   5040
accgtaaaaa ggccgcgttg ctggcgtttt tccataggct ccgcccccct gacgagcatc   5100
acaaaaatcg acgctcaagt cagaggtggc gaaacccgac aggactataa agataccagg   5160
cgtttccccc tggaagctcc ctcgtgcgct ctcctgttcc gaccctgccg cttaccggat   5220
acctgtccgc ctttctccct tcgggaagcg tggcgctttc tcaatgctca cgctgtaggt   5280
atctcagttc ggtgtaggtc gttcgctcca agctgggctg tgtgcacgaa ccccccgttc   5340
agcccgaccg ctgcgcctta tccggtaact atcgtcttga gtccaacccg gtaagacacg   5400
acttatcgcc actggcagca gccactggta acaggattag cagagcgagg tatgtaggcg   5460
gtgctacaga gttcttgaag tggtggccta actacggcta cactagaagg acagtatttg   5520
gtatctgcgc tctgctgaag ccagttacct tcggaaaaag agttggtagc tcttgatccg   5580
gcaaacaaac caccgctggt agcggtggtt tttttgtttg caagcagcag attacgcgca   5640
gaaaaaaagg atctcaagaa gatcctttgt taccaatgct taatcagtga ggcacctatc   5700
tcagcgatct gtctatttcg ttcatccata gttgcctgac tccccgtcgt gtagataact   5760
acgatacggg agggcttacc atctggcccc agtgctgcaa tgataccgcg agacccacgc   5820
tcaccggctc cagatttatc agcaataaac cagccagccg gaagggccga gcgcagaagt   5880
ggtcctgcaa ctttatccgc ctccatccag tctattaatt gttgccggga agctagagta   5940
agtagttcgc cagttaatag tttgcgcaac gttgttgcca ttgctacagg catcgtggtg   6000
tcacgctcgt cgtttggtat ggcttcattc agctccggtt cccaacgatc aaggcgagtt   6060
acatgatccc ccatgttgtg caaaaaagcg gttagctcct tcggtcctcc gatcgttgtc   6120
agaagtaagt tggccgcagt gttatcactc atggttatgg cagcactgca taattctctt   6180
actgtcatgc catccgtaag atgcttttct gtgactggtg agtactcaac caagtcattc   6240
tgagaatagt gtatgcggcg accgagttgc tcttgcccgg cgtcaatacg ggataatacc   6300
gcgccacata gcagaacttt aaaagtgctc atcattggaa aacgttcttc ggggcgaaaa   6360
ctctcaagga tcttaccgct gttgagatcc agttcgatgt aacccactcg tgcacccaac   6420
tgatcttcag catcttttac tttcaccagc gtttctgggt gagcaaaaac aggaaggcaa   6480
aatgccgcaa aaaagggaat aagggcgaca cggaaatgtt gaatactcat actcttcctt   6540
tttcaatatt attgaagcat ttatcagggt tattgtctca tgtccgcgcg tttcctgcat   6600
```

```
cttttaatca aatcccaaga tgtgtataaa ccaccaaact gccaaaaaat gaaaactgtc   6660

gacaagctct gtccgtttgc tggcaactgc aagggtctca atcctatttg taattattga   6720

ataataaaac aattataaat gtcaaatttg tttttatta acgatacaaa ccaaacgcaa   6780

caagaacatt tgtagtatta tctataattg aaaacgcgta gttataatcg ctgaggtaat   6840

atttaaaatc attttcaaat gattcacagt taatttgcga caatataatt ttattttcac   6900

ataaactaga cgccttgtcg tcttcttctt cgtattcctt ctctttttca tttttctctt   6960

cataaaaatt aacatagtta ttatcgtatc catatatgta tctatcgtat agagtaaatt   7020

ttttgttgtc ataaatatat atgtcttttt taatggggtg tatagtaccg ctgcgcatag   7080

tttttctgta atttacaaca gtgctatttt ctggtagttc ttcggagtgt gttgctttaa   7140

ttattaaatt tatataatca atgaatttgg gatcgtcggt tttgtacaat atgttgccgg   7200

catagtacgc agcttcttct agttcaatta caccattttt tagcagcacc ggattaacat   7260

aactttccaa aatgttgtac gaaccgttaa acaaaaacag ttcacctccc ttttctatac   7320

tattgtctgc gagcagttgt ttgttgttaa aaataacagc cattgtaatg agacgcacaa   7380

actaatatca caaactggaa atgtctatca atatatagtt gctctagtta ttaatagtaa   7440

tcaattacgg ggtcattagt tcatagccca tatatggagt tccgcgttac ataacttacg   7500

gtaaatggcc cgcctggctg accgcccaac gacccccgcc cattgacgtc aataatgacg   7560

tatgttccca tagtaacgcc aatagggact ttccattgac gtcaatgggt ggactattta   7620

cggtaaactg cccacttggc agtacatcaa gtgtatcata tgccaagtac gccccctatt   7680

gacgtcaatg acggtaaatg gcccgcctgg cattatgccc agtacatgac cttatgggac   7740

tttcctactt ggcagtacat ctacgtatta gtcatcgcta ttaccatgca tggtcgaggt   7800

gagccccacg ttctgcttca ctctccccat ctcccccccc tccccacccc caattttgta   7860

tttatttatt ttttaattat tttgtgcagc gatgggggcg gggggggggg gggggcgcgc   7920

gccaggcggg gcggggcggg gcgaggggcg gggcggggcg aggcggagag gtgcggcggc   7980

agccaatcag agcggcgcgc tccgaaagtt tccttttatg gcgaggcggc ggcggcggcg   8040

gccctataaa aagcgaagcg cgcggcgggc gggagtcgct gcgacgctgc cttcgccccg   8100

tgccccgctc cgccgccgcc tcgcgccgcc cgccccggct ctgactgacc gcgttactcc   8160

cacaggtgag cgggcgggac ggcccttctc cttcgggctg taattagcgc ttggtttaat   8220

gacggcttgt ttcttttctg tggctgcgtg aaagccttga ggggctccgg gagggccctt   8280

tgtgcggggg gagcggctcg gggctgtccg cggggggacg gctgccttcg ggggggacgg   8340

ggcagggcgg ggttcggctt ctggcgtgtg accggcggct ctagagcctc tgctaaccat   8400

gttcatgcct tcttcttttt cctacagctc ctgggcaacg tgctggttat tgtgctgtct   8460

catcattttg gcaaagaatt ggatcggacc gaaattaata cgactcacta taggggaatt   8520

gtgagcggat aacaattccc cggagttaat ccgggacctt taattcaacc caacacaata   8580

tattatagtt aaataagaat tattatcaaa tcatttgtat attaattaaa atactatact   8640

gtaaattaca ttttatttac aatcaaagga gatataggcc gtca                     8684
```

<210> SEQ ID NO 6
<211> LENGTH: 6526
<212> TYPE: DNA
<213> ORGANISM: artificial
<220> FEATURE:
<223> OTHER INFORMATION: vector comprising sequence encoding for ATPase -continued

<400> SEQUENCE: 6

```
ggggaattgt gagcggataa caattccccg gagttaatcc gggaccttta attcaaccca     60
acacaatata ttatagttaa ataagaatta ttatcaaatc atttgtatat taattaaaat    120
actatactgt aaattacatt ttatttacaa tcaaaggaga tataccatgg cccgcgggaa    180
agccaaggag gagggcagct ggaagaaatt catctggaac tcagagaaga aggagtttct    240
gggcaggacc ggtggcagtt ggtttaagat ccttctattc tacgtaatat tttatggctg    300
cctggctggc atcttcatcg gaaccatcca agtgatgctg ctcaccatca gtgaatttaa    360
gcccacatat caggaccgag tggccccgcc aggattaaca cagattcctc agatccagaa    420
gactgaaatt tcctttcgtc ctaatgatcc caagagctat gaggcatatg tactgaacat    480
agttaggttc ctggaaaagt acaaagattc agcccagagg gatgacatga tttttgaaga    540
ttgtggcgat gtgcccagtg aaccgaaaga acgaggagac tttaatcatg aacgaggaga    600
gcgaaaggtc tgcagattca agcttgaatg gctgggaaat tgctctggat taaatgatga    660
aacttatggc tacaaagagg gcaaaccgtg cattattata aagctcaacc gagttctagg    720
cttcaaacct aagcctccca agaatgagtc cttggagact tacccagtga tgaagtataa    780
cccaaatgtc cttcccgttc agtgcactgg caagcgagat gaagataagg ataaagttgg    840
aaatgtggag tattttggac tgggcaactc ccctggtttt cctctgcagt attatccgta    900
ctatggcaaa ctcctgcagc ccaaatacct gcagcccctg ctggccgtac agttcaccaa    960
tcttaccatg gacactgaaa ttcgcataga gtgtaaggcg tacggtgaga acattgggta   1020
cagtgagaaa gaccgttttc agggacgttt tgatgtaaaa attgaagtta agagctgact   1080
cgagcaccac catcaccatc accatcacta agtgattaac ctcaggtgca ggctgcctat   1140
cagaaggtgg tggctggtgt ggccaatgcc ctggctcaca aataccactg agatcgatct   1200
tttccctctg ccaaaaaatt atggggacat catgaagccc cttgagcatc tgacttctgg   1260
ctaataaagg aaatttattt tcattgcaat agtgtgttgg aattttttgt gtctctcact   1320
cggaaggaca tatgggaggg caaatcattt aaaacatcag aatgagtatt tggtttagag   1380
tttggcaaca tatgcccata tgtaactagc ataacccctt ggggcctcta aacgggtctt   1440
gaggggtttt ttgctgaaag catgcggagg aaattctcct tgaagtttcc ctggtgttca   1500
aagtaaagga gtttgcacca gacgcacctc tgttcactgg tccggcgtat taaaacacga   1560
tacattgtta ttagtacatt tattaagcgc tagattctgt gcgttgttga tttacagaca   1620
attgttgtac gtattttaat aattcattaa atttataatc tttagggtgg tatgttagag   1680
cgaaaatcaa atgattttca gcgtctttat atctgaattt aaatattaaa tcctcaatag   1740
atttgtaaaa taggtttcga ttagtttcaa acaagggttg tttttccgaa ccgatggctg   1800
gactatctaa tggattttcg ctcaacgcca caaaacttgc caaatcttgt agcagcaatc   1860
tagctttgtc gatattcgtt tgtgttttgt tttgtaataa aggttcgacg tcgttcaaaa   1920
tattatgcgc ttttgtattt ctttcatcac tgtcgttagt gtacaattga ctcgacgtaa   1980
acacgttaaa tagagcttgg acatatttaa catcgggcgt gttagcttta ttaggccgat   2040
tatcgtcgtc gtcccaaccc tcgtcgttag aagttgcttc cgaagacgat tttgccatag   2100
ccacacgacg cctattaatt gtgtcggcta acacgtccgc gatcaaattt gtagttgagc   2160
tttttggaat tatttctgat tgcgggcgtt tttgggcggg tttcaatcta actgtgcccg   2220
attttaattc agacaacacg ttagaaagcg atggtgcagg cggtggtaac atttcagacg   2280
gcaaatctac taatggcggc ggtggtggag ctgatgataa atctaccatc ggtggaggcg   2340
```

-continued

```
caggcggggc tggcggcgga ggcggaggcg gaggtggtgg cggtgatgca gacggcggtt   2400
taggctcaaa tgtctcttta ggcaacacag tcggcacctc aactattgta ctggtttcgg   2460
gcgccgtttt tggtttgacc ggtctgagac gagtgcgatt tttttcgttt ctaatagctt   2520
ccaacaattg ttgtctgtcg tctaaaggtg cagcgggttg aggttccgtc ggcattggtg   2580
gagcgggcgg caattcagac atcgatggtg gtggtggtgg tggaggcgct ggaatgttag   2640
gcacgggaga aggtggtggc ggcggtgccg ccggtataat ttgttctggt ttagtttgtt   2700
cgcgcacgat tgtgggcacc ggcgcaggcg ccgctggctg cacaacggaa ggtcgtctgc   2760
ttcgaggcag cgcttggggt ggtggcaatt caatattata attggaatac aaatcgtaaa   2820
aatctgctat aagcattgta atttcgctat cgtttaccgt gccgatattt aacaaccgct   2880
caatgtaagc aattgtattg taaagagatt gtctcaagct cggaacgctg cgctcggtcg   2940
ttcggctgcg gcgagcggta tcagctcact caaaggcggt aatacggtta tccacagaat   3000
caggggataa cgcaggaaag aacatgtgag caaaaggcca gcaaaaggcc aggaaccgta   3060
aaaaggccgc gttgctggcg tttttccata ggctccgccc ccctgacgag catcacaaaa   3120
atcgacgctc aagtcagagg tggcgaaacc cgacaggact ataaagatac caggcgtttc   3180
cccctggaag ctccctcgtg cgctctcctg ttccgaccct gccgcttacc ggatacctgt   3240
ccgcctttct cccttcggga agcgtggcgc tttctcaatg ctcacgctgt aggtatctca   3300
gttcggtgta ggtcgttcgc tccaagctgg gctgtgtgca cgaacccccc gttcagcccg   3360
accgctgcgc cttatccggt aactatcgtc ttgagtccaa cccggtaaga cacgacttat   3420
cgccactggc agcagccact ggtaacagga ttagcagagc gaggtatgta ggcggtgcta   3480
cagagttctt gaagtggtgg cctaactacg gctacactag aaggacagta tttggtatct   3540
gcgctctgct gaagccagtt accttcggaa aaagagttgg tagctcttga tccggcaaac   3600
aaaccaccgc tggtagcggt ggtttttttg tttgcaagca gcagattacg cgcagaaaaa   3660
aaggatctca agaagatcct ttgttaccaa tgcttaatca gtgaggcacc tatctcagcg   3720
atctgtctat ttcgttcatc catagttgcc tgactccccg tcgtgtagat aactacgata   3780
cgggagggct taccatctgg ccccagtgct gcaatgatac cgcgagaccc acgctcaccg   3840
gctccagatt tatcagcaat aaaccagcca gccggaaggg ccgagcgcag aagtggtcct   3900
gcaactttat ccgcctccat ccagtctatt aattgttgcc gggaagctag agtaagtagt   3960
tcgccagtta atagtttgcg caacgttgtt gccattgcta caggcatcgt ggtgtcacgc   4020
tcgtcgtttg gtatggcttc attcagctcc ggttcccaac gatcaaggcg agttacatga   4080
tcccccatgt tgtgcaaaaa agcggttagc tccttcggtc ctccgatcgt tgtcagaagt   4140
aagttggccg cagtgttatc actcatggtt atggcagcac tgcataattc tcttactgtc   4200
atgccatccg taagatgctt ttctgtgact ggtgagtact caaccaagtc attctgagaa   4260
tagtgtatgc ggcgaccgag ttgctcttgc ccggcgtcaa tacgggataa taccgcgcca   4320
catagcagaa ctttaaaagt gctcatcatt ggaaaacgtt cttcggggcg aaaactctca   4380
aggatcttac cgctgttgag atccagttcg atgtaaccca ctcgtgcacc caactgatct   4440
tcagcatctt ttactttcac cagcgtttct gggtgagcaa aaacaggaag gcaaaatgcc   4500
gcaaaaaagg gaataagggc gacacggaaa tgttgaatac tcatactctt cctttttcaa   4560
tattattgaa gcatttatca gggttattgt ctcatgtccg cgcgtttcct gcatctttta   4620
atcaaatccc aagatgtgta taaaccacca aactgccaaa aatgaaaac tgtcgacaag   4680
```

-continued

```
ctctgtccgt ttgctggcaa ctgcaagggt ctcaatccta tttgtaatta ttgaataata   4740

aaacaattat aaatgtcaaa tttgtttttt attaacgata caaaccaaac gcaacaagaa   4800

catttgtagt attatctata attgaaaacg cgtagttata atcgctgagg taatatttaa   4860

aatcattttc aaatgattca cagttaattt gcgacaatat aattttattt tcacataaac   4920

tagacgcctt gtcgtcttct tcttcgtatt ccttctcttt ttcatttttc tcttcataaa   4980

aattaacata gttattatcg tatccatata tgtatctatc gtatagagta aatttttttgt   5040

tgtcataaat atatatgtct tttttaatgg ggtgtatagt accgctgcgc atagtttttc   5100

tgtaatttac aacagtgcta ttttctggta gttcttcgga gtgtgttgct ttaattatta   5160

aatttatata atcaatgaat ttgggatcgt cggttttgta caatatgttg ccggcatagt   5220

acgcagcttc ttctagttca attacaccat tttttagcag caccggatta acataacttt   5280

ccaaaatgtt gtacgaaccg ttaaacaaaa acagttcacc tcccttttct atactattgt   5340

ctgcgagcag ttgtttgttg ttaaaaataa cagccattgt aatgagacgc acaaactaat   5400

atcacaaact ggaaatgtct atcaatatat agttgctcta gttattaata gtaatcaatt   5460

acggggtcat tagttcatag cccatatatg gagttccgcg ttacataact tacggtaaat   5520

ggcccgcctg gctgaccgcc caacgacccc cgcccattga cgtcaataat gacgtatgtt   5580

cccatagtaa cgccaatagg gactttccat tgacgtcaat gggtggacta tttacggtaa   5640

actgcccact tggcagtaca tcaagtgtat catatgccaa gtacgccccc tattgacgtc   5700

aatgacggta aatggcccgc ctggcattat gcccagtaca tgaccttatg ggactttcct   5760

acttggcagt acatctacgt attagtcatc gctattacca tgcatggtcg aggtgagccc   5820

cacgttctgc ttcactctcc ccatctcccc cccctcccca cccccaattt tgtatttatt   5880

tatttttttaa ttattttgtg cagcgatggg ggcggggggg gggggggggc gcgcgccagg   5940

cggggcgggg cggggcgagg ggcggggcgg ggcgaggcgg agaggtgcgg cggcagccaa   6000

tcagagcggc gcgctccgaa agtttccttt tatggcgagg cggcggcggc ggcggcccta   6060

taaaaagcga agcgcgcggc gggcgggagt cgctgcgacg ctgccttcgc cccgtgcccc   6120

gctccgccgc cgcctcgcgc cgcccgcccc ggctctgact gaccgcgtta ctcccacagg   6180

tgagcgggcg ggacggccct tctccttcgg gctgtaatta gcgcttggtt taatgacggc   6240

ttgtttcttt tctgtggctg cgtgaaagcc ttgaggggct ccgggagggc cctttgtgcg   6300

gggggagcgg ctcggggctg tccgcggggg gacggctgcc ttcggggggg acggggcagg   6360

gcggggttcg gcttctggcg tgtgaccggc ggctctagag cctctgctaa ccatgttcat   6420

gccttcttct ttttcctaca gctcctgggc aacgtgctgg ttattgtgct gtctcatcat   6480

tttggcaaag aattggatcg gaccgaaatt aatacgactc actata                  6526
```

<210> SEQ ID NO 7
<211> LENGTH: 5809
<212> TYPE: DNA
<213> ORGANISM: artificial
<220> FEATURE:
<223> OTHER INFORMATION: vector

<400> SEQUENCE: 7

```
ggggaattgt gagcggataa caattccccg gagttaatcc gggaccttta attcaaccca     60

acacaatata ttatagttaa ataagaatta ttatcaaatc atttgtatat taattaaaat    120

actatactgt aaattacatt ttatttacaa tcaaaggaga tataccatgg acaggtggta    180

cctgggcggc agccccaagg gggacgtgga cccgttctac tatgactatg agaccgttcg    240
```

-continued

```
caatgggggc ctgatcttcg ctggactggc cttcatcgtg gggctcctca tcctcctcag    300
cagaagattc cgctgtgggg gcaataagaa gcgcaggcaa atcaatgaag atgagccgta    360
actcgagcac caccatcacc atcaccatca ctaagtgatt aacctcaggt gcaggctgcc    420
tatcagaagg tggtggctgg tgtggccaat gccctggctc acaaatacca ctgagatcga    480
tctttttccc tctgccaaaa attatgggga catcatgaag ccccttgagc atctgacttc    540
tggctaataa aggaaattta ttttcattgc aatagtgtgt tggaattttt tgtgtctctc    600
actcggaagg acatatggga gggcaaatca tttaaaacat cagaatgagt atttggttta    660
gagtttggca acatatgccc atatgtaact agcataaccc cttggggcct ctaaacgggt    720
cttgaggggt tttttgctga aagcatgcgg aggaaattct ccttgaagtt tccctggtgt    780
tcaaagtaaa ggagtttgca ccagacgcac ctctgttcac tggtccggcg tattaaaaca    840
cgatacattg ttattagtac atttattaag cgctagattc tgtgcgttgt tgatttacag    900
acaattgttg tacgtatttt aataattcat taaatttata atctttaggg tggtatgtta    960
gagcgaaaat caaatgattt tcagcgtctt tatatctgaa tttaaatatt aaatcctcaa   1020
tagatttgta aaataggttt cgattagttt caaacaaggg ttgtttttcc gaaccgatgg   1080
ctggactatc taatggattt tcgctcaacg ccacaaaact tgccaaatct tgtagcagca   1140
atctagcttt gtcgatattc gtttgtgttt tgttttgtaa taaaggttcg acgtcgttca   1200
aaatattatg cgcttttgta tttctttcat cactgtcgtt agtgtacaat tgactcgacg   1260
taaacacgtt aaatagagct tggacatatt taacatcggg cgtgttagct ttattaggcc   1320
gattatcgtc gtcgtcccaa ccctcgtcgt tagaagttgc ttccgaagac gatttgcca    1380
tagccacacg acgcctatta attgtgtcgg ctaacacgtc cgcgatcaaa tttgtagttg   1440
agctttttgg aattatttct gattgcgggc gtttttgggc gggtttcaat ctaactgtgc   1500
ccgattttaa ttcagacaac acgttagaaa gcgatggtgc aggcggtggt aacatttcag   1560
acggcaaatc tactaatggc ggcggtggtg gagctgatga taaatctacc atcggtggag   1620
gcgcaggcgg ggctggcggc ggaggcggag gcggaggtgg tggcggtgat gcagacggcg   1680
gtttaggctc aaatgtctct ttaggcaaca cagtcggcac ctcaactatt gtactggttt   1740
cgggcgccgt tttggtttg accggtctga gacgagtgcg attttttttcg tttctaatag   1800
cttccaacaa ttgttgtctg tcgtctaaag gtgcagcggg ttgaggttcc gtcggcattg   1860
gtggagcggg cggcaattca gacatcgatg gtggtggtgg tggtggaggc gctggaatgt   1920
taggcacggg agaaggtggt ggcggcggtg ccgccggtat aatttgttct ggtttagttt   1980
gttcgcgcac gattgtgggc accggcgcag gcgccgctgg ctgcacaacg gaaggtcgtc   2040
tgcttcgagg cagcgcttgg ggtggtggca attcaatatt ataattggaa tacaaatcgt   2100
aaaaatctgc tataagcatt gtaatttcgc tatcgtttac cgtgccgata tttaacaacc   2160
gctcaatgta agcaattgta ttgtaaagag attgtctcaa gctcggaacg ctgcgctcgg   2220
tcgttcggct gcggcgagcg gtatcagctc actcaaaggc ggtaatacgg ttatccacag   2280
aatcagggga taacgcagga aagaacatgt gagcaaaagg ccagcaaaag gccaggaacc   2340
gtaaaaaggc cgcgttgctg gcgtttttcc ataggctccg cccccctgac gagcatcaca   2400
aaaatcgacg ctcaagtcag aggtggcgaa acccgacagg actataaaga taccaggcgt   2460
ttccccctgg aagctccctc gtgcgctctc ctgttccgac cctgccgctt accggatacc   2520
tgtccgcctt tctcccttcg ggaagcgtgg cgctttctca atgctcacgc tgtaggtatc   2580
```

-continued

```
tcagttcggt gtaggtcgtt cgctccaagc tgggctgtgt gcacgaaccc cccgttcagc   2640
ccgaccgctg cgccttatcc ggtaactatc gtcttgagtc caacccggta agacacgact   2700
tatcgccact ggcagcagcc actggtaaca ggattagcag agcgaggtat gtaggcggtg   2760
ctacagagtt cttgaagtgg tggcctaact acggctacac tagaaggaca gtatttggta   2820
tctgcgctct gctgaagcca gttaccttcg gaaaaagagt tggtagctct tgatccggca   2880
aacaaaccac cgctggtagc ggtggttttt ttgtttgcaa gcagcagatt acgcgcagaa   2940
aaaaaggatc tcaagaagat cctttgttac caatgcttaa tcagtgaggc acctatctca   3000
gcgatctgtc tatttcgttc atccatagtt gcctgactcc ccgtcgtgta gataactacg   3060
atacgggagg gcttaccatc tggccccagt gctgcaatga taccgcgaga cccacgctca   3120
ccggctccag atttatcagc aataaaccag ccagccggaa gggccgagcg cagaagtggt   3180
cctgcaactt tatccgcctc catccagtct attaattgtt gccgggaagc tagagtaagt   3240
agttcgccag ttaatagttt gcgcaacgtt gttgccattg ctacaggcat cgtggtgtca   3300
cgctcgtcgt ttggtatggc ttcattcagc tccggttccc aacgatcaag gcgagttaca   3360
tgatccccca tgttgtgcaa aaaagcggtt agctccttcg gtcctccgat cgttgtcaga   3420
agtaagttgg ccgcagtgtt atcactcatg gttatggcag cactgcataa ttctcttact   3480
gtcatgccat ccgtaagatg cttttctgtg actggtgagt actcaaccaa gtcattctga   3540
gaatagtgta tgcggcgacc gagttgctct tgcccggcgt caatacggga taataccgcg   3600
ccacatagca gaactttaaa agtgctcatc attggaaaac gttcttcggg gcgaaaactc   3660
tcaaggatct taccgctgtt gagatccagt tcgatgtaac ccactcgtgc acccaactga   3720
tcttcagcat cttttacttt caccagcgtt tctgggtgag caaaaacagg aaggcaaaat   3780
gccgcaaaaa agggaataag ggcgacacgg aaatgttgaa tactcatact cttccttttt   3840
caatattatt gaagcattta tcagggttat tgtctcatgt ccgcgcgttt cctgcatctt   3900
ttaatcaaat cccaagatgt gtataaacca ccaaactgcc aaaaaatgaa aactgtcgac   3960
aagctctgtc cgtttgctgg caactgcaag ggtctcaatc ctatttgtaa ttattgaata   4020
ataaaacaat tataaatgtc aaatttgttt tttattaacg atacaaacca aacgcaacaa   4080
gaacatttgt agtattatct ataattgaaa acgcgtagtt ataatcgctg aggtaatatt   4140
taaaatcatt ttcaaatgat tcacagttaa tttgcgacaa tataatttta ttttcacata   4200
aactagacgc cttgtcgtct tcttcttcgt attccttctc tttttcattt ttctcttcat   4260
aaaaattaac atagttatta tcgtatccat atatgtatct atcgtataga gtaaattttt   4320
tgttgtcata aatatatatg tcttttttaa tggggtgtat agtaccgctg cgcatagttt   4380
ttctgtaatt tacaacagtg ctattttctg gtagttcttc ggagtgtgtt gctttaatta   4440
ttaaatttat ataatcaatg aatttgggat cgtcggtttt gtacaatatg ttgccggcat   4500
agtacgcagc ttcttctagt tcaattacac catttttttag cagcaccgga ttaacataac   4560
tttccaaaat gttgtacgaa ccgttaaaca aaaacagttc acctcccttt tctatactat   4620
tgtctgcgag cagttgtttg ttgttaaaaa taacagccat tgtaatgaga cgcacaaact   4680
aatatcacaa actggaaatg tctatcaata tatagttgct ctagttatta atagtaatca   4740
attacggggt cattagttca tagcccatat atggagttcc gcgttacata acttacggta   4800
aatggcccgc ctggctgacc gcccaacgac ccccgcccat tgacgtcaat aatgacgtat   4860
gttcccatag taacgccaat agggactttc cattgacgtc aatgggtgga ctatttacgg   4920
taaactgccc acttggcagt acatcaagtg tatcatatgc caagtacgcc ccctattgac   4980
```

```
gtcaatgacg gtaaatggcc cgcctggcat tatgcccagt acatgacctt atgggacttt   5040
cctacttggc agtacatcta cgtattagtc atcgctatta ccatgcatgg tcgaggtgag   5100
ccccacgttc tgcttcactc tccccatctc ccccccctcc ccacccccaa ttttgtattt   5160
atttattttt taattatttt gtgcagcgat gggggcgggg gggggggggg ggcgcgcgcc   5220
aggcggggcg gggcggggcg aggggcgggg cggggcgagg cggagaggtg cggcggcagc   5280
caatcagagc ggcgcgctcc gaaagtttcc ttttatggcg aggcggcggc ggcggcggcc   5340
ctataaaaag cgaagcgcgc ggcgggcggg agtcgctgcg acgctgcctt cgccccgtgc   5400
cccgctccgc cgccgcctcg cgccgcccgc cccggctctg actgaccgcg ttactcccac   5460
aggtgagcgg gcgggacggc ccttctcctt cgggctgtaa ttagcgcttg gtttaatgac   5520
ggcttgtttc ttttctgtgg ctgcgtgaaa gccttgaggg gctccgggag ggccctttgt   5580
gcggggggag cggctcgggg ctgtccgcgg ggggacggct gccttcgggg gggacggggc   5640
agggcggggt tcggcttctg gcgtgtgacc ggcggctcta gagcctctgc taaccatgtt   5700
catgccttct tctttttcct acagctcctg ggcaacgtgc tggttattgt gctgtctcat   5760
cattttggca aagaattgga tcggaccgaa attaatacga ctcactata               5809
```

<210> SEQ ID NO 8
<211> LENGTH: 48
<212> TYPE: DNA
<213> ORGANISM: Artificial Sequence
<220> FEATURE:
<223> OTHER INFORMATION: primer

<400> SEQUENCE: 8
aagggccgtc aaggccacca tgggggacaa gaaagatgac aaggactc 48

<210> SEQ ID NO 9
<211> LENGTH: 44
<212> TYPE: DNA
<213> ORGANISM: Artificial Sequence
<220> FEATURE:
<223> OTHER INFORMATION: primer

<400> SEQUENCE: 9
tatggcccat gaggcctagt agtaggtttc cttctccacc caac 44

<210> SEQ ID NO 10
<211> LENGTH: 37
<212> TYPE: DNA
<213> ORGANISM: Artificial Sequence
<220> FEATURE:
<223> OTHER INFORMATION: vector

<400> SEQUENCE: 10
atacgtctca catggcccgc gggaaagcca aggagga 37

<210> SEQ ID NO 11
<211> LENGTH: 42
<212> TYPE: DNA
<213> ORGANISM: Artificial Sequence
<220> FEATURE:
<223> OTHER INFORMATION: vector

<400> SEQUENCE: 11
atacgtctcc tcgagtcagc tcttaacttc aatttttaca tc 42

<210> SEQ ID NO 12

<211> LENGTH: 24
<212> TYPE: DNA
<213> ORGANISM: Artificial Sequence
<220> FEATURE:
<223> OTHER INFORMATION: vector

<400> SEQUENCE: 12
ctgccatgga caggtggtac ctgg 24

<210> SEQ ID NO 13
<211> LENGTH: 34
<212> TYPE: DNA
<213> ORGANISM: Artificial Sequence
<220> FEATURE:
<223> OTHER INFORMATION: vector

<400> SEQUENCE: 13
tatctcgagt tacggctcat cttcattgat ttgc 34

<210> SEQ ID NO 14
<211> LENGTH: 1013
<212> TYPE: PRT
<213> ORGANISM: Rattus norvegicus

<400> SEQUENCE: 14

```
Met Gly Asp Lys Lys Asp Asp Lys Ser Ser Pro Lys Lys Ser Lys Ala
1               5                   10                  15

Lys Glu Arg Arg Asp Leu Asp Asp Leu Lys Lys Glu Val Ala Met Thr
            20                  25                  30

Glu His Lys Met Ser Val Glu Glu Val Cys Arg Lys Tyr Asn Thr Asp
        35                  40                  45

Cys Val Gln Gly Leu Thr His Ser Lys Ala Gln Glu Ile Leu Ala Arg
    50                  55                  60

Asp Gly Pro Asn Ala Leu Thr Pro Pro Pro Thr Thr Pro Glu Trp Val
65                  70                  75                  80

Lys Phe Cys Arg Gln Leu Phe Gly Gly Phe Ser Ile Leu Leu Trp Ile
                85                  90                  95

Gly Ala Ile Leu Cys Phe Leu Ala Tyr Gly Ile Gln Ala Gly Thr Glu
            100                 105                 110

Asp Asp Pro Ser Gly Asp Asn Leu Tyr Leu Gly Ile Val Leu Ala Ala
        115                 120                 125

Val Val Ile Ile Thr Gly Cys Phe Ser Tyr Tyr Gln Glu Ala Lys Ser
    130                 135                 140

Ser Lys Ile Met Glu Ser Phe Lys Asn Met Val Pro Gln Gln Ala Leu
145                 150                 155                 160

Val Ile Arg Glu Gly Glu Lys Met Gln Val Asn Ala Glu Glu Val Val
                165                 170                 175

Val Gly Asp Leu Val Glu Ile Lys Gly Gly Asp Arg Val Pro Ala Asp
            180                 185                 190

Leu Arg Ile Ile Ser Ala His Gly Cys Lys Val Asp Asn Ser Ser Leu
        195                 200                 205

Thr Gly Glu Ser Glu Pro Gln Thr Arg Ser Pro Asp Cys Thr His Asp
    210                 215                 220

Asn Pro Leu Glu Thr Arg Asn Ile Thr Phe Phe Ser Thr Asn Cys Val
225                 230                 235                 240

Glu Gly Thr Ala Arg Gly Val Val Val Ala Thr Gly Asp Arg Thr Val
                245                 250                 255

Met Gly Arg Ile Ala Thr Leu Ala Ser Gly Leu Glu Val Gly Lys Thr
```

-continued

```
            260                 265                 270

Pro Ile Ala Ile Glu Ile Glu His Phe Ile Gln Leu Ile Thr Gly Val
        275                 280                 285

Ala Val Phe Leu Gly Val Ser Phe Phe Ile Leu Ser Leu Ile Leu Gly
    290                 295                 300

Tyr Thr Trp Leu Glu Ala Val Ile Phe Leu Ile Gly Ile Ile Val Ala
305                 310                 315                 320

Asn Val Pro Glu Gly Leu Leu Ala Thr Val Thr Val Cys Leu Thr Leu
                325                 330                 335

Thr Ala Lys Arg Met Ala Arg Lys Asn Cys Leu Val Lys Asn Leu Glu
            340                 345                 350

Ala Val Glu Thr Leu Gly Ser Thr Ser Thr Ile Cys Ser Asp Lys Thr
        355                 360                 365

Gly Thr Leu Thr Gln Asn Arg Met Thr Val Ala His Met Trp Phe Asp
    370                 375                 380

Asn Gln Ile His Glu Ala Asp Thr Thr Glu Asp Gln Ser Gly Thr Ser
385                 390                 395                 400

Phe Asp Lys Ser Ser His Thr Trp Val Ala Leu Ser His Ile Ala Gly
                405                 410                 415

Leu Cys Asn Arg Ala Val Phe Lys Gly Gly Gln Asp Asn Ile Pro Val
            420                 425                 430

Leu Lys Arg Asp Val Ala Gly Asp Ala Ser Glu Ser Ala Leu Leu Lys
        435                 440                 445

Cys Ile Glu Leu Ser Ser Gly Ser Val Lys Leu Met Arg Glu Arg Asn
    450                 455                 460

Lys Lys Val Ala Glu Ile Pro Phe Asn Ser Thr Asn Lys Tyr Gln Leu
465                 470                 475                 480

Ser Ile His Glu Thr Glu Asp Pro Asn Asp Asn Arg Tyr Leu Leu Val
                485                 490                 495

Met Lys Gly Ala Pro Glu Arg Ile Leu Asp Arg Cys Ala Thr Ile Leu
            500                 505                 510

Leu Gln Gly Lys Glu Gln Pro Leu Asp Glu Glu Met Lys Glu Ala Phe
        515                 520                 525

Gln Asn Ala Tyr Leu Glu Leu Gly Gly Leu Gly Glu Arg Val Leu Gly
    530                 535                 540

Phe Cys His Tyr Tyr Leu Pro Glu Glu Gln Phe Pro Lys Gly Phe Ala
545                 550                 555                 560

Phe Asp Cys Asp Asp Val Asn Phe Thr Thr Asp Asn Leu Cys Phe Val
                565                 570                 575

Gly Leu Met Ser Met Ile Asp Pro Pro Arg Ala Ala Val Pro Asp Ala
            580                 585                 590

Val Gly Lys Cys Arg Ser Ala Gly Ile Lys Val Ile Met Val Thr Gly
        595                 600                 605

Asp His Pro Ile Thr Ala Lys Ala Ile Ala Lys Gly Val Gly Ile Ile
    610                 615                 620

Ser Glu Gly Asn Glu Thr Val Glu Asp Ile Ala Ala Arg Leu Asn Ile
625                 630                 635                 640

Pro Val Ser Gln Val Asn Pro Arg Asp Ala Lys Ala Cys Val Ile His
                645                 650                 655

Gly Thr Asp Leu Lys Asp Phe Thr Ser Glu Gln Ile Asp Glu Ile Leu
            660                 665                 670

Gln Asn His Thr Glu Ile Val Phe Ala Arg Thr Ser Pro Gln Gln Lys
        675                 680                 685
```

```
Leu Ile Ile Val Glu Gly Cys Gln Arg Gln Gly Ala Ile Val Ala Val
    690                 695                 700

Thr Gly Asp Gly Val Asn Asp Ser Pro Ala Leu Lys Lys Ala Asp Ile
705                 710                 715                 720

Gly Val Ala Met Gly Ile Ala Gly Ser Asp Val Ser Lys Gln Ala Ala
                725                 730                 735

Asp Met Ile Leu Leu Asp Asp Asn Phe Ala Ser Ile Val Thr Gly Val
            740                 745                 750

Glu Glu Gly Arg Leu Ile Phe Asp Asn Leu Lys Lys Ser Ile Ala Tyr
        755                 760                 765

Thr Leu Thr Ser Asn Ile Pro Glu Ile Thr Pro Phe Leu Leu Phe Ile
    770                 775                 780

Met Ala Asn Ile Pro Leu Pro Leu Gly Thr Ile Thr Ile Leu Cys Ile
785                 790                 795                 800

Asp Leu Gly Thr Asp Met Val Pro Ala Ile Ser Leu Ala Tyr Glu Ala
                805                 810                 815

Ala Glu Ser Asp Ile Met Lys Arg Gln Pro Arg Asn Pro Arg Thr Asp
            820                 825                 830

Lys Leu Val Asn Glu Arg Leu Ile Ser Met Ala Tyr Gly Gln Ile Gly
        835                 840                 845

Met Ile Gln Ala Leu Gly Gly Phe Phe Ser Tyr Phe Val Ile Leu Ala
    850                 855                 860

Glu Asn Gly Phe Leu Pro Gly Asn Leu Val Gly Ile Arg Leu Asn Trp
865                 870                 875                 880

Asp Asp Arg Thr Val Asn Asp Leu Glu Asp Ser Tyr Gly Gln Gln Trp
                885                 890                 895

Thr Tyr Glu Gln Arg Lys Val Val Glu Phe Thr Cys His Thr Ala Phe
            900                 905                 910

Phe Val Ser Ile Val Val Val Gln Trp Ala Asp Leu Ile Ile Cys Lys
        915                 920                 925

Thr Arg Arg Asn Ser Val Phe Gln Gln Gly Met Lys Asn Lys Ile Leu
    930                 935                 940

Ile Phe Gly Leu Phe Glu Glu Thr Ala Leu Ala Ala Phe Leu Ser Tyr
945                 950                 955                 960

Cys Pro Gly Met Asp Val Ala Leu Arg Met Tyr Pro Leu Lys Pro Ser
                965                 970                 975

Trp Trp Phe Cys Ala Phe Pro Tyr Ser Phe Leu Ile Phe Val Tyr Asp
            980                 985                 990

Glu Ile Arg Lys Leu Ile Leu Arg Arg Asn Pro Gly Gly Trp Val Glu
        995                 1000                1005

Lys Glu Thr Tyr Tyr
    1010
```

<210> SEQ ID NO 15
<211> LENGTH: 964
<212> TYPE: PRT
<213> ORGANISM: Sus scrofa

<400> SEQUENCE: 15

```
Met Gly Asp Lys Lys Asp Asp Lys Gly Ser Pro Lys Lys Gly Lys Gly
1               5                   10                  15

Thr Lys Asp Arg Arg Asp Leu Asp Asp Leu Lys Lys Glu Val Ala Met
            20                  25                  30

Thr Glu His Lys Met Ser Val Glu Glu Val Cys Arg Lys Tyr Asn Thr
```

-continued

```
        35                  40                  45

Asp Cys Val Gln Gly Leu Thr His Ser Lys Ala Gln Glu Ile Leu Ala
    50                  55                  60

Arg Asp Gly Pro Asn Ala Leu Thr Pro Pro Pro Thr Thr Pro Glu Trp
65                  70                  75                  80

Val Lys Phe Cys Arg Gln Leu Phe Gly Gly Phe Ser Ile Leu Leu Trp
                85                  90                  95

Ile Gly Ala Ile Leu Cys Phe Leu Ala Tyr Gly Ile Gln Ala Gly Thr
            100                 105                 110

Glu Asp Asp Pro Ser Gly Asp Asn Leu Tyr Leu Gly Ile Val Leu Ala
        115                 120                 125

Ala Val Val Ile Ile Thr Gly Cys Phe Ser Tyr Tyr Gln Glu Ala Lys
    130                 135                 140

Ser Ser Lys Ile Met Glu Ser Phe Lys Asn Met Val Pro Gln Gln Ala
145                 150                 155                 160

Leu Val Ile Arg Glu Gly Glu Lys Met Gln Val Asn Ala Glu Glu Val
                165                 170                 175

Val Val Gly Asp Leu Val Glu Ile Lys Gly Gly Asp Arg Val Pro Ala
            180                 185                 190

Asp Leu Arg Ile Ile Ser Ala His Gly Cys Lys Val Asp Asn Ser Ser
        195                 200                 205

Leu Thr Gly Glu Ser Glu Pro Gln Thr Arg Ser Pro Asp Cys Thr His
    210                 215                 220

Asp Asn Pro Leu Glu Thr Arg Asn Ile Thr Phe Phe Ser Thr Asn Cys
225                 230                 235                 240

Val Glu Gly Thr Ala Arg Gly Val Val Val Ala Thr Gly Asp Arg Thr
                245                 250                 255

Val Met Gly Arg Ile Ala Thr Leu Ala Ser Gly Leu Glu Val Gly Lys
            260                 265                 270

Thr Pro Ile Ala Ile Glu Ile Glu His Phe Ile Gln Leu Ile Thr Gly
        275                 280                 285

Val Ala Val Phe Leu Gly Val Ser Phe Phe Ile Leu Ser Leu Ile Leu
    290                 295                 300

Gly Tyr Thr Trp Leu Glu Ala Val Ile Phe Leu Ile Gly Ile Ile Val
305                 310                 315                 320

Ala Asn Val Pro Glu Gly Leu Leu Ala Thr Val Thr Val Cys Leu Thr
                325                 330                 335

Leu Thr Ala Lys Arg Met Ala Arg Lys Asn Cys Leu Val Lys Asn Leu
            340                 345                 350

Glu Ala Val Glu Thr Leu Gly Ser Thr Ser Thr Ile Cys Ser Asp Lys
        355                 360                 365

Thr Gly Thr Leu Thr Gln Asn Arg Met Thr Val Ala His Met Trp Phe
    370                 375                 380

Asp Asn Gln Ile His Glu Ala Asp Thr Thr Glu Asp Gln Ser Gly Thr
385                 390                 395                 400

Ser Phe Asp Lys Ser Ser His Thr Trp Val Ala Leu Ser His Ile Ala
                405                 410                 415

Gly Leu Cys Asn Arg Ala Val Phe Lys Gly Gly Gln Asp Asn Ile Pro
            420                 425                 430

Val Leu Lys Arg Asp Val Ala Gly Asp Ala Ser Glu Ser Ala Leu Leu
        435                 440                 445

Lys Cys Ile Glu Leu Ser Ser Gly Ser Val Lys Leu Met Arg Glu Arg
    450                 455                 460
```

-continued

```
Asn Lys Lys Val Ala Glu Ile Pro Phe Asn Ser Thr Asn Lys Tyr Gln
465                 470                 475                 480

Leu Ser Ile His Glu Thr Glu Asp Pro Asn Asp Asn Arg Tyr Leu Leu
                485                 490                 495

Val Met Lys Gly Ala Pro Glu Arg Ile Leu Asp Arg Cys Ser Thr Ile
            500                 505                 510

Leu Leu Gln Gly Lys Glu Gln Pro Leu Asp Glu Glu Met Lys Glu Ala
        515                 520                 525

Phe Gln Asn Ala Tyr Leu Glu Leu Gly Gly Leu Gly Glu Arg Val Leu
    530                 535                 540

Gly Phe Cys His Tyr Tyr Leu Pro Glu Glu Gln Phe Pro Lys Gly Phe
545                 550                 555                 560

Ala Phe Asp Cys Asp Asp Val Asn Phe Thr Thr Asp Asn Leu Cys Phe
                565                 570                 575

Val Gly Leu Met Ser Met Ile Asp Pro Pro Arg Ala Ala Val Pro Asp
            580                 585                 590

Ala Val Gly Lys Cys Arg Ser Ala Gly Ile Lys Val Ile Met Val Thr
        595                 600                 605

Gly Asp His Pro Ile Thr Ala Lys Ala Ile Ala Lys Gly Val Gly Ile
    610                 615                 620

Ile Ser Glu Gly Asn Glu Thr Val Glu Asp Ile Ala Ala Arg Leu Asn
625                 630                 635                 640

Ile Pro Val Ser Gln Val Asn Pro Arg Asp Ala Lys Ala Cys Val Ile
                645                 650                 655

His Gly Thr Asp Leu Lys Asp Phe Thr Ser Glu Gln Ile Asp Glu Ile
            660                 665                 670

Leu Gln Asn His Thr Glu Ile Val Phe Ala Arg Thr Ser Pro Gln Gln
        675                 680                 685

Lys Leu Ile Ile Val Glu Gly Cys Gln Arg Gln Gly Ala Ile Val Ala
    690                 695                 700

Val Thr Gly Asp Gly Val Asn Asp Ser Pro Ala Leu Lys Lys Ala Asp
705                 710                 715                 720

Ile Gly Val Ala Met Gly Ile Ala Gly Ser Asp Val Ser Lys Gln Ala
                725                 730                 735

Ala Asp Met Ile Leu Leu Asp Asp Asn Phe Ala Ser Ile Val Thr Gly
            740                 745                 750

Val Glu Glu Gly Arg Leu Ile Phe Asp Asn Leu Lys Lys Ser Ile Ala
        755                 760                 765

Tyr Thr Leu Thr Ser Asn Ile Pro Glu Ile Thr Pro Phe Leu Leu Phe
    770                 775                 780

Ile Met Ala Asn Ile Pro Leu Pro Leu Gly Thr Ile Thr Ile Leu Cys
785                 790                 795                 800

Ile Asp Leu Gly Thr Asp Met Val Pro Ala Ile Ser Leu Ala Tyr Glu
                805                 810                 815

Ala Ala Glu Ser Asp Ile Met Lys Arg Gln Pro Arg Asn Pro Arg Thr
            820                 825                 830

Asp Lys Leu Val Asn Glu Arg Leu Ile Ser Met Ala Tyr Gly Gln Ile
        835                 840                 845

Gly Met Ile Gln Ala Leu Gly Gly Phe Phe Ser Tyr Phe Val Ile Leu
    850                 855                 860

Ala Glu Asn Gly Phe Leu Pro Ser Asn Leu Val Gly Ile Arg Leu Asn
865                 870                 875                 880
```

-continued

| | | | | | | | | | | | | | | | |
|---|---|---|---|---|---|---|---|---|---|---|---|---|---|---|---|
| Trp | Asp | Asp | Arg | Thr | Val | Asn | Asp | Leu | Glu | Asp | Ser | Tyr | Gly | Gln | Gln |
| | | | | 885 | | | | | 890 | | | | | 895 | |
| Trp | Thr | Tyr | Glu | Gln | Arg | Lys | Val | Val | Glu | Phe | Thr | Cys | His | Thr | Ala |
| | | | 900 | | | | | 905 | | | | | 910 | | |
| Phe | Phe | Val | Ser | Ile | Val | Val | Val | Gln | Trp | Ala | Asp | Leu | Ile | Ile | Cys |
| | | 915 | | | | | 920 | | | | | 925 | | | |
| Lys | Thr | Arg | Arg | Asn | Ser | Val | Phe | Gln | Gln | Gly | Met | Lys | Asn | Lys | Ile |
| | 930 | | | | | 935 | | | | | 940 | | | | |
| Leu | Ile | Phe | Gly | Leu | Phe | Arg | Arg | Asn | Pro | Gly | Gly | Trp | Val | Glu | Lys |
| 945 | | | | | 950 | | | | | 955 | | | | | 960 |
| Glu | Thr | Tyr | Tyr | | | | | | | | | | | | |

DIAGNOSIS OF A NEUROLOGICAL DISEASE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 310159_406_SEQUENCE_LISTING.txt. The text file is 44 KB, was created on Jul. 15, 2015, and is being submitted electronically via EFS-Web.

BACKGROUND

Technical Field

The present invention relates to a method for diagnosing a disease, comprising the step detecting in a sample an autoantibody binding to the alpha 3 subunit of the human neuronal Na(+)/K(+) ATPase, an isolated and/or recombinant polypeptide comprising the alpha 3 subunit of the human neuronal Na(+)/K(+) ATPase, a use of a membrane-associated human Na(+)/K(+) ATPase or a variant thereof for the diagnosis of a disease, an isolated and/or recombinant polypeptide comprising the alpha 3 subunit of the human neuronal Na(+)/K(+) ATPase or a variant thereof, for use in the treatment of a disease, an autoantibody binding to said polypeptide and a method for isolating such autoantibody, a pharmaceutical composition, medical or diagnostic device or test kit comprising the polypeptide.

Description of the Related Art

Developing diagnostic systems for neurological disorders is a continuing challenge in biomedical science, not in the least because many symptoms encountered may be accounted for by a huge variety of causes including genetically-inherited diseases, drug abuse, malnutrition, infection, injury, psychiatric illness, immunological defects and cancer. Moreover, it may be difficult to distinguish between symptoms indicating the onset of a disease that requires the medical practitioner to take rapid action and those regularly occurring due to old age.

The importance of an early diagnosis cannot be overemphasized. Many neurodegenerative disorders, most prominently Alzheimer's and Parkinson's diseases, cannot be cured, but drugs are available that may be used to slow down their progression. The earlier the diagnosis, the better the chances to exploit the spectrum of available drugs to the full benefit of the patient.

Notwithstanding the need for an early diagnosis, it is equally important to ensure that results are sufficiently reliable as the basis for the treatment regime chosen subsequently lest the patient be misdiagnosed. For example, patients suffering from the autoimmune disorder referred to as hashimoto encephalitis have repeatedly been diagnosed as having Alzheimer's' disease. Such patients may be denied appropriate treatment and they continue to suffer, although administration of readily available drugs, such as cortisone in the case of hashimoto encephalitis, would be likely to ameliorate their symptoms. In addition, many drugs have severe side-effects and should be prescribed only if the clinician in charge has ascertained, for the sake of the patient, that the benefits will far outweigh any adverse effects.

Patients seeking medical attention from a neurologist frequently have unspecific symptoms that may be associated with a plethora of diseases. For example, in a case reported in the literature, a patient suffering from ataxia, dysphagia and dysarthria on account of a genetically determined mitochondrial metabolic disorder (Danielsson, O., Jonasson, J., and Landtblom, A.-M., Sensory ataxic neuropathy with dysarthria/dysphagia and ophthalmoplegia (SANDO). Two case reports. Acta Myol. December 2011; 30(3): 188-190).

By contrast, a group of patients suffering from a set of symptoms comprising similar manifestations, were shown to have a tauopathy inflicted by autoantibodies (Sabater, L., Gaig, C., Gelpi, E., Bataller, L., Lewerenz, J., Torres-Vega, E., Contreras, A., Giometto, B., Compta, Y., Embid, C., Vilaseca, I., Iranzo, A., Santamaría, J., Dalmau, J., and Graus, F., A novel non-rapid-eye movement and rapid-eye-movement parasomnia with sleep breathing disorder associated with antibodies to IgLON5: a case series, characterization of the antigen, and post-mortem study, Lancet Neurol. 2014 Apr. 2)

Ataxia and, more generally, movement disorders may also be associated with or even caused by numerous other disorders such as stroke, brain tumor, multiple sclerosis, alcoholism, prescription and recreational drugs, radiation poisoning, Vitamin B12 deficiency and hypothyroidism.

In a recent case, a new neurological disorder has been observed that is associated with visual impairment, ataxia, dysarthria, dysphagia and spastic tetraparesis and adenocarcinoma. As far as the inventors are aware, such a disorder has not yet been reported in the literature.

In case a neurologist sees a patient with numerous unspecific symptoms, they will strive to gather any kind of information regarding the cause, even if definitive diagnosis is beyond feasibility. For example, if it can be established that the symptoms are accounted for by a neurodegenerative disorder, this will help rule out various counter-productive treatment regimes. Consequently, there is considerable demand for assays for diagnosing neurological conditions associated with unspecific symptoms such as those described throughout this application.

Therefore, a problem underlying the present invention is to provide an agent and a method for diagnosing a novel neurological disease characterized by one or more symptoms from the group comprising visual impairment, ataxia, dysarthria, dysphagia and spastic tetraparesis, preferably accompanied by a tumor, more preferably an adenocarcinoma.

Another problem underlying the present invention is to provide an autoantibody that, when found in a liquid sample taken from a patient, indicates that said patient is suffering from a neurological disease characterized by visual impairment, ataxia, dysarthria, dysphagia and spastic tetraparesis, preferably accompanied by a tumor, more preferably an adenocarcinoma.

The problem underlying the present invention is solved by the subject-matter of the attached independent and dependent claims.

BRIEF SUMMARY

In a first aspect, the problem underlying the present invention is solved by a method for diagnosing a disease, comprising the step detecting in a sample an autoantibody binding to the alpha 3 subunit of the human neuronal Na(+)/K(+) ATPase.

In a preferred embodiment of the first aspect, the sample is a bodily fluid comprising antibodies, preferably selected from the group comprising whole-blood, serum, CSF, and saliva.

In a second aspect, the problem underlying the present invention is solved by an isolated and/or recombinant polypeptide comprising the alpha 3 subunit of the human neuronal Na(+)/K(+) ATPase or a variant thereof.

In a preferred embodiment of the second aspect, the polypeptide is immobilized.

In a third aspect the problem underlying the present invention is solved by a use of a human neuronal Na(+)/K(+) ATPase or a variant thereof for the diagnosis of a disease, preferably comprising the step detecting autoantibodies binding to said human neuronal Na(+)/K(+) ATPase or variant thereof.

In a fourth aspect the problem underlying the present invention is solved by an isolated and/or recombinant polypeptide comprising the alpha 3 subunit of the human neuronal Na(+)/K(+) ATPase or a variant thereof, preferably in an immobilized form, for use in the treatment of a disease.

In a $5^{th}$ aspect the problem underlying the present invention is solved by an autoantibody, preferably an isolated autoantibody, binding to a polypeptide of the second aspect, wherein the autoantibody is preferably in complex with said polypeptide.

In a $6^{th}$ aspect the problem underlying the present invention is solved by a method for isolating an autoantibody binding to the polypeptide according to second aspect, comprising the steps a) contacting a sample comprising the autoantibody with the polypeptide according to second aspect under conditions compatible with formation of a complex, wherein said autoantibody binds to said polypeptide,
b) isolating the complex formed in step a),
c) dissociating the complex isolated in step b), and
d) separating the autoantibody from the polypeptide.

In a $7^{th}$ aspect the problem underlying the present invention is solved by a pharmaceutical composition comprising the polypeptide according to the second aspect.

In an $8^{th}$ aspect the problem underlying the present invention is solved by a medical or diagnostic device comprising the polypeptide according to the second aspect.

In a $9^{th}$ aspect the problem underlying the present invention is solved by a test kit for the diagnosis of a disease, comprising the polypeptide according to the second aspect.

In a preferred embodiment of the $9^{th}$ aspect, the test kit further comprises a means for detecting the complex comprising the autoantibody binding to the polypeptide according to second aspect and the polypeptide according to second aspect.

In a preferred embodiment of any aspect of the present invention, the disease is selected from the group comprising cancer, preferably adenocarcinoma, and a neurological disorder, preferably characterized by two or more, preferably all, symptoms selected from the group comprising mixed movement disorder, acute decline of visual performance, dysarthria and dysphagia.

In a preferred embodiment of any aspect of the present invention, the autoantibody is an autoantibody binding to the alpha 3 subunit of the human neuronal Na(+)/K(+) ATPase.

In a preferred embodiment of any aspect of the present invention, the polypeptide is provided in the form of a cell comprising a nucleic acid encoding said polypeptide or in the form of a tissue comprising said polypeptide.

BRIEF DESCRIPTION OF THE SEVERAL VIEWS OF THE DRAWINGS

The present invention is further illustrated by the following figures and non-limiting sequences and examples from which further features, embodiments, aspects and advantages of the present invention may be taken.

FIG. 4A: Patient CSF was incubated in a 10-fold dilution on HEK293 cells expressing recombinant subunits of the Na+/K+ ATPase. A3: Alpha 3 subunit, B1: Beta 1 subunit, G: gamma subunit. Cells were fixed with acetone or 1% formalin. FIG. 4B: Neutralization of immunofluorescence reaction on neuronal tissues. Patient serum in a 1000-fold dilution was preincubated with extracts of HEK293 cells transfected with the Na+/K+ alpha 3 subunit or with empty vector as control.

DETAILED DESCRIPTION

Figure 1:
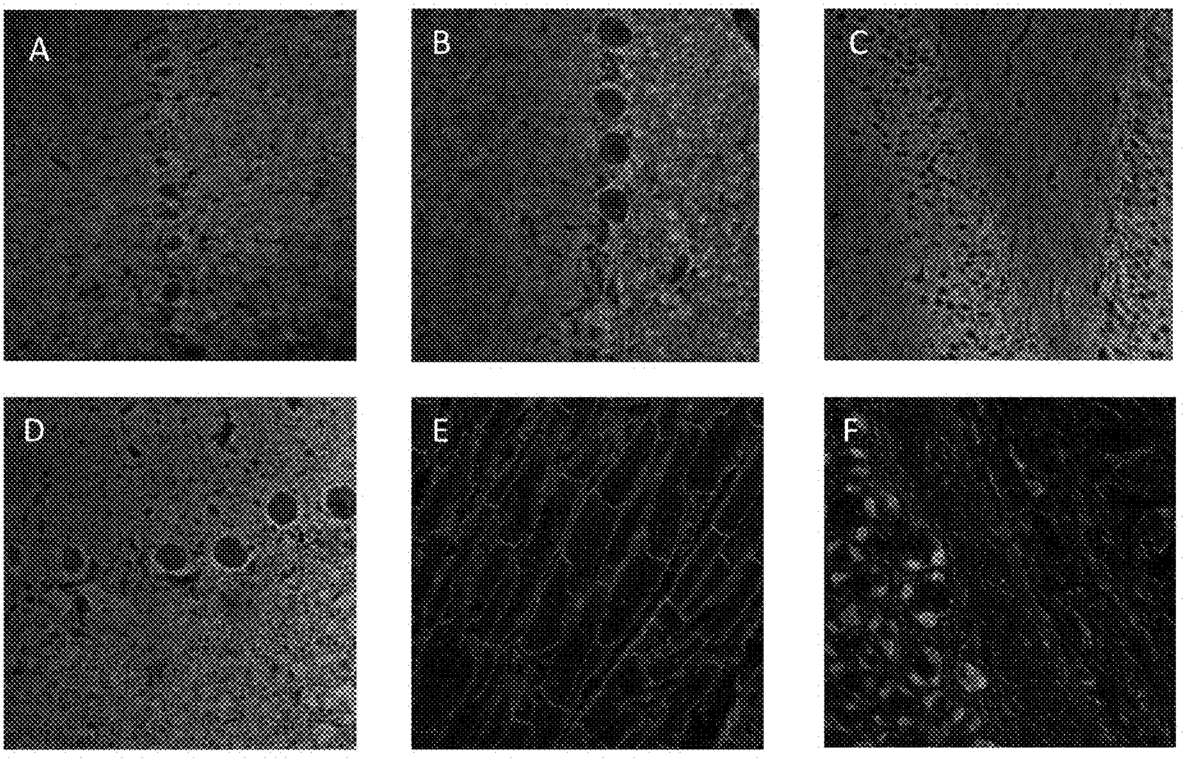
FIG. 1 depicts the results of immunofluorescence staining of central nervous tissues, heart and stomach. Croysections were incubated with patient serum diluted 320-fold. Nuclei were counterstained by incubation with TO-PRO-3 iodide. A: rat cerebellum, B: primate cerebellum, C: rat hippocampus, D: pig cerebellum, E: primate heart, F: primate stomach.

The present invention is based on the inventors' surprising finding that autoantibodies binding to human neuronal membrane-associated ATPases exist that are associated with the neurological disease characterized by visual impairment, ataxia, dysarthria, dysphagia and spastic tetraparesis.

Furthermore, the present invention is based on the inventors' surprising finding that the emergence of autoantibodies binding to human neuronal membrane-associated ATPases indicates an increased likelihood of adenocarcinoma.

Without wishing to be bound to this theory, the inventors hypothesize that the patient's immune system attacks human neuronal ATPases in neurons or other cells vital for the nervous system to the effect that such cells die and synaptic transmission is impaired.

The present invention relates to a polypeptide comprising a mammalian ATPase, more preferably a human ATPase, more preferably a mammalian or human neuronal ATPase or a variant thereof, which polypeptide is referred to, throughout the application as "inventive polypeptide". In a preferred embodiment, said ATPase is a membrane-associated Na(+)/K(+) ATPase. In a most preferred embodiment, the polypeptide comprises the alpha 3 subunit of the human neuronal Na(+)/K(+) ATPase encoded by the data base code P13637. Throughout this application, any data base codes cited refers to the UniProtKB/Swiss-Prot data base, more specifically the version accessible on-line on May 2, 2014.

However, the teachings of the present invention may not only be carried out using polypeptides, in particular a polypeptide comprising the alpha 3 subunit of the human neuronal Na(+)/K(+) ATPase encoded by the data base code P13637, or nucleic acids having the exact sequences referred to in this application explicitly, for example by function, name, sequence or accession number, or implicitly, but also using variants of such polypeptides or nucleic acids In a preferred embodiment, the term "variant", as used herein, may refer to at least one fragment of the full length sequence referred to, more specifically one or more amino acid or nucleic acid sequence which is, relative to the full-length sequence, truncated at one or both termini by one or more amino acids. Such a fragment comprises or encodes for a peptide having at least 6, 7, 8, 10, 12, 15, 20, 25, 50, 75, 100, 150 or 200 successive amino acids of the original sequence or a variant thereof. The total length of the variant may be at least 6, 7, 8, 9, 10, 11, 12, 20, 25, 30, 40, 50, 60, 70, 80, 90, 100 or more amino acids.

In another preferred embodiment, the term "variant" relates not only to at least one fragment, but also a polypeptide or a fragment thereof comprising amino acid sequences that are at least 40, 50, 60, 70, 75, 80, 85, 90, 92, 94, 95, 96, 97, 98 or 99% identical to the reference amino acid sequence referred to or the fragment thereof, wherein amino acids other than those essential for the biological activity, for example the ability of an antigen to bind to an (auto)antibody, or the fold or structure of the polypeptide are deleted or substituted and/or one or more such essential amino acids are replaced in a conservative manner and/or amino acids are added such that the biological activity of the polypeptide is preserved. The state of the art comprises various methods that may be used to align two given nucleic acid or amino acid sequences and to calculate the degree of identity, see for example Arthur Lesk (2008), Introduction to bioinformatics, Oxford University Press, 2008, 3rd edition. In a preferred embodiment, the ClustalW software (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007). Clustal W and Clustal X version 2.0. Bioinformatics, 23, 2947-2948) is used using default settings.

In a preferred embodiment, variants may, in addition, comprise chemical modifications, for example isotopic labels or covalent modifications such as glycosylation, phosphorylation, acetylation, decarboxylation, citrullination, hydroxylation and the like. The person skilled in the art is familiar with methods to modify polypeptides. Any modification is designed such that it does not abolish the biological activity of the variant.

Moreover, variants may also be generated by fusion with other known polypeptides or variants thereof and comprise active portions or domains, preferably having a sequence identity of at least 70, 75, 80, 85, 90, 92, 94, 95, 96, 97, 98 or 99% when aligned with the active portion of the reference sequence, wherein the term "active portion", as used herein, refers to an amino acid sequence, which is less than the full length amino acid sequence or, in the case of a nucleic acid sequence, codes for less than the full length amino acid sequence, respectively, and/or is a variant of the natural sequence, but retains at least some of the biological activity.

In a preferred embodiment, the term "variant" of a nucleic acid comprises nucleic acids the complementary strand of which hybridizes, preferably under stringent conditions, to the reference or wild type nucleic acid. Stringency of hybridization reactions is readily determinable by one of ordinary skilled in the art, and in generally is an empirical calculation dependent on probe length, washing temperature and salt concentration. In general longer probes require higher temperatures for proper annealing, while shorter probes less so. Hybridization generally depends on the ability of denatured DNA to reanneal to complementary strands present in an environment below their melting temperature: The higher the degree of desired homology between the probe and hybridizable sequence, the higher the relative temperature which may be used. As a result it follows that higher relative temperatures would tend to make the reaction conditions more stringent, while lower temperature less so. For additional details and explanation of stringency of hybridization reactions, see Ausubel, F. M. (1995), Current Protocols in Molecular Biology. John Wiley & Sons, Inc. Moreover, the person skilled in the art may follow the instructions given in the manual Boehringer Mannheim GmbH (1993) The DIG System Users Guide for Filter Hybridization, Boehringer Mannheim GmbH, Mannheim, Germany and in Liebl, W., Ehrmann, M., Ludwig, W., and Schleifer, K. H. (1991) International Journal of Systematic Bacteriology 41: 255-260 on how to identify DNA sequences by means of hybridization. In a preferred embodiment, stringent conditions are applied for any hybridization, i.e. hybridization occurs only if the probe is 70% or more identical to the target sequence. Probes having a lower degree of identity with respect to the target sequence may hybridize, but such hybrids are unstable and will be removed in a washing step under stringent conditions, for example lowering the concentration of salt to 2×SSC or, optionally and subsequently, to 0.5×SSC, while the temperature is, in order of increasing preference, approximately 50° C.-68° C., approximately 52° C.-68° C., approximately 54° C.-68° C., approximately 56° C.-68° C., approximately 58° C.-68° C., approximately 60° C.-68° C., approximately 62° C.-68° C., approximately 64° C.-68° C., approximately 66° C.-68° C. In a particularly preferred embodiment, the temperature is approximately 64° C.-68° C. or approximately 66° C.-68° C. It is possible to adjust the concentration of salt to 0.2×SSC or even 0.1×SSC. Nucleic acid sequences having a degree of identity with respect to the reference or wild type sequence of at least 70, 80, 90, 91, 92, 93, 94, 95, 96, 97, 98, 99% may be isolated. In a preferred embodiment, the term variant of a nucleic acid sequence, as used herein, refers to any nucleic acid sequence that encodes the same amino acid sequence and variants thereof as the reference nucleic acid sequence, in line with the degeneracy of the genetic code.

The variant of the polypeptide has biological activity. In a preferred embodiment such biological activity is the ability to bind specifically to the IgG2 class autoantibodies found in patients suffering from a disorder selected from the group comprising paraneoplastic disorders, neurological disorders, more preferably neurological paraneoplastic disorders, most preferably a neurological disorder characterized by one or more symptoms, preferably all symptoms, selected from the group comprising mixed movement disorder, acute decline of visual performance, dysarthria and dysphagia, and cancer, more preferably adenocarcinoma The inventive polypeptide, which comprises a human neuronal Na(+)/K(+) ATPase, more specifically the alpha 3 subunit thereof, or a variant thereof, when used to carry out the teachings of the present invention, may be provided in any form and at any degree of purification, from tissues or cells comprising said polypeptide in an endogenous form, more preferably cells overexpressing the polypeptide, crude or enriched lysates of such cells, to purified and/or isolated polypeptide which is essentially pure. In a preferred embodiment, the polypeptide is a native polypeptide, wherein the term "native polypeptide", as used herein, refers to a folded polypeptide, more preferably to a folded polypeptide purified from tissues or cells, more preferably from mammalian cells or tissues, optionally from non-recombinant tissues or cells. In another preferred embodiment, the polypeptide is a recombinant protein, wherein the term "recombinant", as used herein, refers to a polypeptide produced using genetic engineering approaches at any stage of the production process, for example by fusing a nucleic acid encoding the polypeptide to a strong promoter for overexpression in cells or tissues or by engineering the sequence of the polypeptide itself. The person skilled in the art is familiar with methods for engineering nucleic acids and polypeptides encoded (for example, described in Sambrook, J., Fritsch, E. F. and Maniatis, T. (1989), Molecular Cloning, CSH or in Brown T. A. (1986), Gene Cloning—an introduction, Chapman & Hall) and for producing and purifying native or recombinant polypeptides (for example Handbooks "Strategies for Protein Purification", "Antibody Purification", "Purifying Challenging Proteins", "Recombinant Protein Purification", "Affinity Chromatography", "Ion Exchange Chromatography", "Gel Filtration (Size Exclusion Chromatography)", "Hydrophobic Interaction Chromatography", "Multimodal Chromatography" (2009/2010), published by GE Healthcare Life Sciences, and in Burgess, R. R., Deutscher, M. P. (2009), Guide to Protein Purification). In a preferred embodiment, a polypeptide is pure if at least 60, 70, 80, 90, 95 or 99 percent of the polypeptide in the respective sample consists of said polypeptide as judged by SDS polyacrylamide gel electrophoresis followed by Coomassie blue staining and visual inspection.

If the inventive polypeptide comprising a human neuronal Na(+)/K(+) ATPase or a variant thereof is provided in the form of tissue, it is preferred that the tissue is from mammalian brain, for example human, rat, primate, donkey, mouse, goat, horse, sheep, pig or cow brain. If said polypeptide is provided in the form of a non-recombinant cell, it is preferred that the cell is a neuron, preferably a hippocampal neuron or a cell from the neuropil of a mammal, for example rat, human, primate, donkey, mouse, goat, horse, sheep, pig or cow. If a cell lysate is used, it is preferred that the cell lysate comprises the membranes associated with the surface of the cell. If said polypeptide is provided in the form of a recombinant cell, it is preferred that the recombinant cell is a eukaryotic cell such as a yeast cell, more preferably a cell from a multicellular eukaryote such as a plant, mammal, frog or insect, most preferably from a mammal, for example rat, human, primate, donkey, mouse, goat, horse, sheep, pig or cow. For example, the cell may be a HEK293 cell transfected with a nucleic acid functionally encoding the inventive polypeptide. The person skilled in the art is familiar with methods for preparing, transfecting and culturing such cells, for example those described in Phelan, M. C. (2001), Basic Techniques in Mammalian Cell Tissue Culture, John Wiley.

The polypeptide used to carry out the inventive teachings, including any variants, is preferably designed such that it comprises epitopes recognized by and/or binds specifically to autoantibodies binding to a mammalian, preferably human neuronal ATPase, more specifically the alpha 3 subunit of human neuronal Na(+)/K(+) ATPase, or variants thereof, more preferably taken from patients suffering from the novel neurological disorder identified by the inventors. In one embodiment, such polypeptide comprises a stretch of 6, 7, 8, 9, 10, 11, 12, 20, 25, 30, 40, 50, 60, 70, 80, 90, 100 or more, preferably at least 9 but no more than 16, consecutive amino acids from the human neuronal Na+/K+/ATPase. The person skilled in the art is familiar with guidelines used to design peptides having sufficient immunogenicity, for example those described in Jackson, D. C., Fitzmaurice, C. J., Brown, L. E., Zeng, W. (1999), Preparation and properties of totally synthetic immunogenes, Vaccine Volume 18, Issues 3-4, September 1999, Pages 355-361; and Black, M., Trent, A., Tirrell, M. and Olive, C. (2010), Advances in the design and delivery of peptide subunit vaccines with a focus on Toll-like receptor agonists, Expert Rev Vaccines, 2010 February; 9(2): 157-173. Briefly, it is desirable that the peptide meets as many as possible of the following requirements: (a) it has a high degree of hydrophilicity, (b) it comprises one or more residues selected from the group comprising aspartate, proline, tyrosine and phenylalanine, (c) is has, for higher specificity, no or little homology with other known peptides or polypeptides, (d) it needs to be sufficiently soluble and (e) it comprises no glycosylation or phosphorylation sites unless required for specific reasons. Alternatively, bioinformatics approaches may be followed, for example those described by Moreau, V., Fleury, C., Piquer, D., Nguyen, C., Novali, N., Villard, S., Laune, D., Granier, C. and Molina, F. (2008), PEPOP: Computational design of immunogenic peptides, BMC Bioinformatics 2008, 9:71.

The inventive polypeptide, which comprises the human neuronal Na(+)/K(+) ATPase or a variant thereof, when used according to the present invention, may be provided in any kind of conformation. For example, the polypeptide may be an essentially unfolded, a partially or a fully folded polypeptide. In a preferred embodiment, the polypeptide is folded in the sense that the epitopes that are essential for the binding to the inventive autoantibody, or the protein or variant thereof in its entirety, adopt the fold adopted by the native protein in its natural environment. The person skilled in the art is familiar with methods suitable to determine whether or not a polypeptide is folded and if it is, which structure it has, for example limited proteolysis, NMR spectroscopy, CD spectroscopy or X-ray crystallography (see for example Banaszak L. J. (2008), Foundations of Structural Biology, Academics Press, or Teng Q. (2013), Structural Biology: Practical Applications, Springer), preferably multidimensional NMR spectroscopy is used.

The inventive polypeptide may be a fusion protein which comprises amino acid sequences other than those taken from mammalian ATPases, in particular a C-terminal or N-terminal tag, preferably a C-terminal tag, which is, in a preferred embodiment, as used herein, an additional sequence motif or polypeptide having a function that has some biological or physical function and may, for example, be used to purify, immobilize, precipitate or identify the inventive polypeptide. In a more preferred embodiment, the tag is a sequence or domain capable of binding specifically to a ligand, for example a tag selected from the group comprising His tags, thioredoxin, maltose binding protein, glutathione-S-transferase, a fluorescence tag, for example from the group comprising green fluorescent protein.

The inventive polypeptide may be an immobilized polypeptide. In a preferred embodiment, the term "immobilized", as used herein, refers to a molecule bound to a solid carrier insoluble in an aqueous solution, more preferably via a covalent bond, electrostatic interactions, encapsulation or entrapment, for example by denaturing a globular polypeptide in a gel, or via hydrophobic interactions, most preferably via one or more covalent bonds. Various suitable carriers, for example paper, polystyrene, metal, silicon or glass surfaces, microfluidic channels, membranes, beads such as magnetic beads, column chromatography media, biochips, polyacrylamide gels and the like have been described in the literature, for example in Kim, D., and Herr, A. E. (2013), Protein immobilization techniques for microfluidic assays, Biomicrofluidics 7(4), 041501. This way, the immobilized molecule, together with the insoluble carrier, may be separated from an aqueous solution in a straightforward manner, for example by filtration, centrifugation or decanting. An immobilized molecule may be immobilized in a reversible or irreversible manner. For example, the immobilization is reversible if the molecule interacts with the carrier via ionic interactions that can be masked by addition of a high concentration of salt or if the molecule is bound via a cleavable covalent bond such as a disulphide bridge which may be cleaved by addition of thiol-containing reagents. By contrast, the immobilization is irreversible if the molecule is tethered to the carrier via a covalent bond that cannot be cleaved in aqueous solution, for example a bond formed by reaction of an epoxide group and an amine group as frequently used to couple lysine side chains to affinity columns. The protein may be indirectly immobilized, for example by immobilizing an antibody or other entity having affinity to the molecule, followed by formation of a complex to the effect that the molecule-antibody complex is immobilized. Various ways to immobilize molecules are described in the literature, for example in Kim, D., Herr, and A. E. (2013), Protein immobilization techniques for microfluidic assays, Biomicrofluidics 7(4), 041501. In addition, various reagents and kits for immobilization reactions are commercially available, for example from Pierce Biotechnology.

It is essential that the sample used for the diagnosis in line with the present invention comprises immunoglobulins. Typically the sample of a bodily fluid comprises a representative set of the entirety of the subject's immunoglobulins. However, the sample, once provided, may be subjected to further processing which may include fractionation, centrifugation, enriching or isolating the entirety of immunoglobulins or any immunoglobulin class of the subject, which may affect the relative distribution of immunoglobulins of the various classes.

The reagents, devices, methods and uses described throughout this application may be used for the diagnosis of a disease selected from the group comprising paraneoplastic disorders, neurological disorders, more preferably paraneoplastic neurological syndrome, most preferably a neurological disorder characterized by one or more symptoms, preferably all symptoms, selected from the group comprising mixed movement disorder, acute decline of visual performance, dysarthria and dysphagia, and cancer, more preferably adenocarcinoma.

In a preferred embodiment, the term "diagnosis", as used herein, refers to any kind of procedure aiming obtain information instrumental in the assessment whether a patient suffers or is likely or more likely than the average or a comparative subject, the latter preferably having similar symptoms, to suffer in the future from certain a disease or disorder in the past, at the time of the diagnosis or in the future, to find out how the disease is progressing or is likely to progress in the future or to evaluate the responsiveness of a patient with regard to a certain treatment, for example the administration of immunosuppressive drugs, drugs slowing down the progress of a neurodegenerative disease or anti-cancer drugs. In other words, the term "diagnosis" comprises not only diagnosing, but also prognosticating and/or monitoring the course of a disease or disorder.

In many cases the mere detection, in other words determining whether or not detectable levels of the antibody are present in the sample, is sufficient for the diagnosis. If the autoantibody can be detected, this will be information instrumental for the clinician's diagnosis and indicates an increased likelihood that the patient suffers from one or more diseases selected from the group comprising paraneoplastic disorders, neurological disorders, more preferably paraneoplastic neurological syndrome, most preferably a neurological disorder characterized by one or more symptoms, preferably all symptoms, selected from the group comprising mixed movement disorder, acute decline of visual performance, dysarthria and dysphagia, and cancer, more preferably adenocarcinoma. In an embodiment, the relative concentration of the antibody in the serum, compared to the level that may be found in the average healthy subject, may be determined. While in many cases it may be sufficient to determine whether or not autoantibodies are present in the sample, the method carried out to obtain information instrumental for the diagnosis may involve determining whether the concentration is at least 10, preferably 20, 25, 50, 100, 200, 500, 1000, 10000 or 100000 times higher than the concentration found in the average healthy subject.

The person skilled in the art will appreciate that a clinician does usually not conclude whether or not the patient suffers or is likely to suffer from a disease, condition or disorders solely on the basis of a single diagnostic parameter, but needs to take into account other aspects, for example the presence of other autoantibodies, markers, blood parameters, clinical assessment of the patient's symptoms or the results of medical imaging or other noninvasive methods such as polysomnography, to arrive at a conclusive diagnosis. See Baenkler H. W. (2012), General aspects of autoimmune diagnostics, in Renz, H., Autoimmune diagnostics, 2012, de Gruyter, page 3. The value of a diagnostic agent or method may also reside the possibility to rule out one disease, thus allowing for the indirect diagnosis of another.

Therefore, the term "diagnosis" does preferably not imply that the diagnostic methods or agents according to the present invention will be definitive and sufficient to finalize the diagnosis on the basis of a single test, let alone parameter, but may refer to a contribution to what is referred to as a "differential diagnosis", i.e. a systematic diagnostic procedure considering the likelihood of a range of possible conditions on the basis of a range of diagnostic parameters. Consequently, the inventive method, polypeptide or use, optionally for determining whether a patient suffers from the neurological disorder characterized by one or more symptoms, preferably all symptoms, selected from the group comprising mixed movement disorder, acute decline of visual performance, dysarthria and dysphagia, or suffers from cancer, preferably adenocarcinoma, may comprise obtaining a sample from a patient, preferably a human patient, determining whether an autoantibody binding to the alpha 3 subunit of human neuronal Na+/K+ ATPase is present in said sample, wherein said determining is performed by contacting the sample with the inventive polypeptide and detecting whether binding occurs between said polypeptide and said autoantibody, preferably using a labeled secondary antibody, more preferably using a method from the group comprising radioimmunoassay, Western blot, line blot, ELISA, indirect and immunofluorescence, wherein said autoantibody binds to said polypeptide if present in the sample, and diagnosing the patient as suffering or being more likely to suffer from said neurological disorder or cancer if the autoantibody was determined to be present in the sample.

The term "diagnosis" may also refer to a method or agent used to distinguish between two or more conditions associated with similar or identical symptoms, for example ataxia caused by an autoimmune defect and other forms of ataxia associated with neurodegenerative diseases, or for singling out a subgroup or specific disease from a spectrum of related disorders. In a preferred embodiment, the spectrum of disorders is the paraneoplastic neurological syndrome.

The term "diagnosis" may also refer to a method or agent used to choose the most promising treatment regime for a patient, preferably a patient having one or more symptoms selected from the group comprising mixed movement disorder, acute decline of visual performance, dysarthria and dysphagia or an adenocarcinoma. In other words, the method or agent may relate to selecting a treatment regimen for a subject. For example, the detection of autoantibodies may indicate that an immunosuppressive therapy is to be selected, which may include administrating to the patient one or more immunosuppressive drugs.

The present invention relates to a complex comprising an (auto)antibody binding to the inventive polypeptide. Such a complex may be used or detected as part of a method for diagnosing a disease. A liquid sample comprising antibodies from a subject may be used to practice the method. Such a liquid sample may be any bodily fluid comprising a representative set of antibodies from the subject, preferably a sample comprising antibodies of the IgG immunoglobulin class from the subject, more preferably from the group comprising IgG1, IgG2 and IgG4 subclasses, most preferably from the IgG4 subclass. For example, a sample may be cerebrospinal fluid (CSF), blood or blood serum, lymph, interstitial fluid and is preferably serum or CSF, more preferably serum.

The step contacting a liquid sample comprising antibodies with the inventive polypeptide may be carried out by incubating an immobilized form of said polypeptide in the presence of the sample comprising antibodies under conditions that are compatible with the formation of the complex comprising said polypeptide and an antibody, preferably an autoantibody, binding to the inventive polypeptide. The liquid sample, then depleted of antibodies binding to the inventive polypeptide may be removed subsequently, followed by one or more washing steps. Finally the complex comprising the antibody and the polypeptide may be detected. In a preferred embodiment, the term "conditions compatible with the formation of the complex" are conditions that allow for the specific antigen-antibody interactions to build up the complex comprising the polypeptide an the antibody. In a preferred embodiment such conditions may comprise incubating the polypeptide in sample diluted 1:100 in PBS buffer for 30 minutes at 25° C. In a preferred embodiment, the term "autoantibody", as used herein, refers to an antibody binding specifically to an endogenous molecule of the animal, preferably mammal, which produces said autoantibody, wherein the level of such antibody is more preferably elevated compared the average of any other antibodies binding specifically to such an endogenous molecule. In a most preferred embodiment, the autoantibody is an autoantibody binding to the alpha 3 subunit from human neuronal Na(+)/K/+) ATPase. Such an autoantibody may be isolated from samples taken from patients suffering from the neurological disorder characterized by two or more, preferably all symptoms selected from the group comprising mixed movement disorder, acute decline of visual performance, dysarthria and dysphagia.

In a preferred embodiment, the detection of the complex for the prognosis, diagnosis, methods or test kit according to the present invention comprises the use of a method selected from the group comprising immunodiffusion techniques, immunoelectrophoretic techniques, light scattering immunoassays, light scattering immunoassays, agglutination techniques, labeled immunoassays such as those from the group comprising radiolabeled immunoassay, enzyme immunoassays, chemiluminscence immunoassays, and immunofluorescence techniques. The person skilled in the art is familiar with these methods, which are also described in the state of the art, for example in Zane, H. D. (2001), Immunology—Theoretical & Practical Concepts in Laboratory Medicine, W. B. Saunders Company, in particular in Chapter 14.

Alternatively, a sample comprising tissue comprising the inventive polypeptide rather than a liquid sample may be used. The tissue sample is preferably from a tissue expressing endogenous human neuronal (Na+/K+) ATPase. Such a sample, which may be in the form of a tissue section fixed on a carrier, for example a glass slide for microscopic analysis, may then be contacted with the inventive antibody, preferably autoantibody, binding to the inventive polypeptide. The antibody is preferably labeled to allow for distinction from endogenous antibodies binding to the inventive polypeptide, so that newly formed complexes may be detected and, optionally, quantified. If the amount of complexes formed is lower than the amount found in a sample taken from a healthy subject, the subject from whom the sample examined has been taken is likely to suffer from a disease.

Any data demonstrating the presence or absence of the complex comprising the antibody and the inventive polypeptide may be correlated with reference data. For example, detection of said complex indicates that the patient who provided the sample analyzed has suffered, is suffering or is likely to suffer in the future from one or more diseases selected from the group comprising paraneoplastic disorders, neurological disorders, more preferably neurological paraneoplastic disorders, most preferably a neurological disorder characterized by one or more symptoms, preferably all symptoms, selected from the group comprising mixed movement disorder, acute decline of visual performance, dysarthria and dysphagia, and cancer, more preferably adenocarcinoma. If a patient has been previously diagnosed and the method for obtaining diagnostically relevant information is run again, the amount of complex detected in both runs may be correlated to find out about the progression of the disease and/or the success of a treatment. For example, if the amount of complex is found to increase, it may be concluded that the disorder is progressing, likely to manifest in the future and/or that any treatment attempted is unsuccessful.

In a preferred embodiment, a microplate, membrane ELISA, dot blot, or line blot is used to carry out the diagnostic method according to the invention. The person skilled in the art is familiar with the experimental setup, which is described in the state of the art (Raoult, D., and Dasch, G. A. (1989), The line blot: an immunoassay for monoclonal and other antibodies. Its application to the serotyping of gram-negative bacteria. J. Immunol. Methods, 125 (1-2), 57-65; WO2013041540). Briefly, the one or more antigen of interest, in the case of the present invention the inventive polypeptide, may be attached to a carrier, for example nitrocellulose membrane, often in combination with additional antigens and controls. The nitrocellulose carrier is subsequently exposed to a sample comprising antibodies such as diluted serum. If the sample comprises an antibody binding to the antigen, a complex is formed which may be detected, preferably by incubation with a secondary antibody binding to the constant region of the first antibody, which secondary antibody comprises a detectable label, for example a radioactive isotope, a fluorescent dye or, in a preferred embodiment, an active enzyme fused or linked to the secondary antibody, such as alkaline phosphatase, which may be readily assayed using chromogenic substrates followed by simple visual examination. Suitable reagents, devices and software packages are commercially available, for example from EUROIMMUN, Lübeck, Germany.

In another preferred embodiment, the prognosis, diagnosis, methods or test kit in line with the inventive teachings contemplate the use of indirect immunofluorescence. The person skilled in the art is familiar with such techniques and the preparation of suitable samples, which are described in the state of the art (U.S. Pat. No. 4,647,543; Voigt, J., Krause, C., Rohwäder, E, Saschenbrecker, S., Hahn, M., Danckwardt, M., Feirer, C., Ens, K, Fechner, K, Barth, E, Martinetz, T., and Stöcker, W. (2012), Automated Indirect Immunofluorescence Evaluation of Antinuclear Autoantibodies on HEp-2 Cells," Clinical and Developmental Immunology, vol. 2012, doi:10.1155/2012/65105; Bonilla, E., Francis, L., Allam, F., et al., Immuno-fluorescence microscopy is superior to fluorescent beads for detection of antinuclear antibody reactivity in systemic lupus erythematosus patients, Clinical Immunology, vol. 124, no. 1, pp. 18-21, 2007). Briefly, a carrier, such as a cover glass for use in microscopy, is coated with cells or tissue sections comprising the antigen, in the case of the present invention the polypeptide comprising one or more sequences of human neuronal Na(+)/K(+) ATPase or a variant thereof. The carrier comprising the antigen is exposed to a patient sample comprising antibodies such as diluted serum. If the sample comprises an antibody binding to the antigen, the resulting complex may be detected, preferably by incubation with a secondary antibody comprising a fluorescent dye such as fluorescein, followed by visual examination using fluorescence microscopy. Suitable reagents, devices and software packages are commercially available, for example from EUROIMMUN, Lübeck, Germany.

A sample from a patient suffering from or suspected to suffer from a disease selected from the group comprising paraneoplastic disorders, neurological disorders, more preferably neurological paraneoplastic disorders, most preferably a neurological disorder characterized by one or more symptoms, preferably all symptoms, selected from the group comprising mixed movement disorder, acute decline of visual performance, dysarthria and dysphagia, and cancer, more preferably adenocarcinoma, may be subjected to a test determining only whether an autoantibody binding to human neuronal Na(+)/K(+) ATPase is present, but it is preferred that diagnostic methods, tests, devices and the like contemplate determining the presence of autoantibodies against a variety of antigens relating to neurological autoimmune disease or variants thereof, for example Hu, Yo, Ri, CV2, PNMA1, PNMA2, DNER/Tr, ARHGAP26, ITPR1, CARPVIII, Zic4, Sox1, MAG, MP0, MBP, GAD65, amphiphysin, recoverin, GABA A receptor, GABA B receptor, glycine receptor, gephyrin, IgLON5, DPPX, aquaporin-4, MOG, NMDA receptor, AMPA receptors, GRM1, GRM5, LGI1 and CASPR2. Therefore, the method, use, kit, device or the like according to the present invention may comprise two or more, preferably three, four, five or more antigens or variants thereof selected from the group comprising Hu, Yo, Ri, CV2, PNMA1, PNMA2, DNER/Tr, ARHGAP26, ITPR1, CARPVIII, Zic4, Sox1, MAG, MP0, MBP, GAD65, amphiphysin, recoverin, GABA A receptor, GABA B receptor, glycine receptor, gephyrin, IgLON5, DPPX, aquaporin-4, MOG, NMDA receptor, AMPA receptors, GRM1, GRM5, LGI1 and CASPR2, which antigens are preferably immobilized, for example on a line blot.

According to the teachings of the present invention, an antibody, preferably an autoantibody binding to the inventive polypeptide used for the diagnosis of a disease is provided. The person skilled in the art is familiar with methods for purifying antibodies, for example those described in Hermanson, G. T., Mallia, A. K., and Smith, P. K. (1992), Immobilized Affinity Ligand Techniques, San Diego: Academic Press. Briefly, an antigen binding specifically to the antibody of interest, which antigen is the inventive polypeptide, is immobilized and used to purify, via affinity chromatography, the antibody of interest from an adequate source. A liquid sample comprising antibodies from a patient suffering from the neurological disorder identified by the inventors may be used as the source.

According to the invention, an antibody, for example an autoantibody, is provided that is capable of binding specifically to the inventive polypeptide. In a preferred embodiment, the term "antibody", as used herein, refers to any immuoglobulin-based binding moieties, more preferably one comprising at least one immunoglobulin heavy chain and one immunoglobulin light chain, including, but not limited to monoclonal and polyclonal antibodies as well as variants of an antibody, in particular fragments, which binding moieties are capable of binding to the respective antigen, more preferably binding specifically to it. In a preferred embodiment, the term "binding specifically", as used herein, means that the binding is stronger than a binding reaction characterized by a dissociation constant of $1\times10^{-5}$ M, more preferably $1\times10^{-7}$ M, more preferably $1\times10^{-8}$ M, more preferably $1\times10^{-9}$ M, more preferably $1\times10^{-10}$ M, more preferably $1\times10^{-11}$ M, more preferably $1\times10^{-12}$ M, as determined by surface plasmon resonance using Biacore equipment at 25° C. in PBS buffer at pH 7. The antibody may be isolated or in a mixture comprising further antibodies, polypeptides, metabolites, cells and the like. In case the antibody is an autoantibody, it may be part of an autoantibody preparation which is heterogeneous or may be a homogenous autoantibody, wherein a heterogeneous preparation comprises a plurality of different autoantibody species as obtainable by preparation from the sera of human donors, for example by affinity chromatography using the immobilized antigen to purify any autoantibody capable of binding to said antigen. Preferably the antibody is an autoantibody, more preferably an autoantibody from the IgG class, most preferably from the group of subclasses comprising IgG1, IgG2 and IgG4, in particular IgG2. In another preferred embodiment, the antibody is a mammalian antibody, more preferably a primate antibody, most preferably a human antibody. The antibody may be glycosylated or non-glycosylated. The person skilled in the art is familiar with methods that may be used for the identification, production and purification of antibodies and variants thereof, for examples those described in EP 2 423 226 A2 and references therein. The antibody may be used as a diagnostic agent, by itself, or in combination, for example in complex with the inventive polypeptide.

The present invention provides a method for isolating an antibody, preferably an autoantibody, binding to the inventive polypeptide, comprising the steps a) contacting a sample comprising the antibody with the inventive polypeptide such that a complex is formed, b) isolating the complex formed in step a), c) dissociating the complex isolated in step b), and d) separating the antibody from the inventive polypeptide. A sample from a patient suffering from the novel neurological disorder identified by the inventors may be used as the source of antibody. Alternatively the antibody may be a recombinant antibody. It is preferred that the polypeptide is immobilized, for example on the matrix of a column suitable for affinity chromatography or on a magnetic bead, since it is straightforward to separate the complex comprising the polypeptide and the antibody in step b) if such is the case. Subsequently, the antibody may be separated from the immobilized antigen in step c), for example by eluting the antibody by addition of an excess of non-immobilized antigen or by adding an agent interfering with intramolecular interactions, for example guanidinium chloride or sodium chloride at a high concentration, the latter if that electrostatic interactions are essential to maintain the complex. One or more washing steps may be included to increase the purity of the complex and the sensitivity and/or specificity of the assay whenever the complex is formed as part of detection or purification methods. The person skilled in the art is familiar with methods to carry out each of these steps. Suitable methods are described in the state of the art, for example in the Handbooks "Affinity chromatography", "Strategies for Protein Purification" and "Antibody Purification" (2009/2010), published by GE Healthcare Life Sciences, and in in Philips, Terry, M., Analytical techniques in immunochemistry, 1992, Marcel Dekker, Inc.

The invention provides a pharmaceutical composition comprising the inventive polypeptide, which composition is preferably suitable for administration to a subject, preferably a mammalian subject, more preferably to a human. Such a pharmaceutical composition may comprise a pharmaceutically acceptable carrier. The pharmaceutical composition may, for example, be administered orally, parenterally, by inhalation spray, topically, by eyedrops, rectally, nasally, buccally, vaginally or via an implanted reservoir, wherein the term "parentally", as used herein, comprises subcutaneous, intracutaneous, intravenous, intramuscular, intra-articular, intrasynovial, instrasternal, intrathecal, intralesional and intracranial injection or infusion techniques. The pharmaceutical composition may be provided in suitable dosage forms, for example capsules, tablets and aqueous suspensions and solutions, preferably in sterile form. It may be used in a method of treatment of a disease, which method comprises administering an effective amount of the inventive polypeptide to a subject.

Within the scope of the present invention, a medical or diagnostic device comprising the inventive (auto)antibody and/or the inventive polypeptide is provided. Preferably such a medical or diagnostic device comprises the inventive polypeptide in a form that allows contacting it with an aqueous solution, more preferably the liquid human sample, in a straightforward manner. In particular, the inventive polypeptide comprising may be immobilized on the surface of a carrier, which carrier comprises, but is not limited to glass plates or slides, biochips, microtiter plates, beads, for example magnetic beads, chromatography columns, membranes or the like. Exemplary medical devices include line blots, microplates and biochips. In addition to the inventive polypeptide, the medical or diagnostic device may comprise additional polypeptides, for example positive or negative controls or known other antigens binding to autoantibodies of diagnostic value, particularly those related other diseases associated with one or more symptoms selected from the group comprising mixed movement disorder, acute decline of visual performance, dysarthria and dysphagia.

The inventive teachings provide a kit for diagnosing a disease associated with one or more symptoms selected from the group comprising mixed movement disorder, acute decline of visual performance, dysarthria and dysphagia. Such a kit may comprise instructions detailing how to use the kit and a means for contacting the inventive polypeptide with a bodily fluid sample from a subject, preferably a human subject, for example a line blot, wherein the inventive polypeptide is immobilized on the line blot. Furthermore, the kit may comprise a positive control, for example a batch of autoantibody or recombinant antibody known to bind to the inventive polypeptide and a negative control, for example a protein having no detectable affinity to the inventive polypeptide such as bovine serum albumin. Finally, such a kit may comprise a standard solution of the antibody or antigen for preparing a calibration curve.

In a preferred embodiment, the kit comprises a means for detecting an antibody, more preferably an autoantibody, binding to the inventive polypeptide, preferably by detecting a complex comprising the inventive polypeptide and an antibody binding to the inventive polypeptide. Such means is preferably an agent that binds to said complex and modifies the complex or carries a label such that makes the complex detectable. For example, said means may be a labeled antibody binding to said polypeptide, at a binding site other than the binding site recognized by the primary antibody or to a constant region of the primary antibody. Alternatively, said means may be a secondary antibody binding to the constant region of the autoantibody, preferably a secondary antibody specific for mammalian IgG class antibodies, more preferably mammalian IgG2 class antibodies. Alternatively, said means may be a crosslinking reagent chemically linking the antibody and the inventive polypeptide, so the complex may be identified on account of its increased molecular weight, for example by SDS PAGE followed by Coomassie staining or size-exclusion chromatography. A multitude of methods and means for detecting such a complex have been described in the state of the art, for example in Philips, Terry, M., Analytical techniques in immunochemistry, 1992, Marcel Dekker, Inc.

The inventive polypeptide may be provided in the form of a cell comprising and/or expressing a nucleic acid encoding said polypeptide. If a nucleic acid comprising a sequence that encodes for the inventive polypeptide or variant thereof is used, such a nucleic acid may be an unmodified nucleic acid. In a preferred embodiment, the nucleic acid is a nucleic acid that, as such, does not occur in nature and comprises, compared to natural nucleic acid, at least one modification, for example an isotopic content or chemical modifications, for example a methylation, sequence modification, label or the like indicative of synthetic origin. In a preferred embodiment, the nucleic acid is a recombinant nucleic acid or part or a nucleic acid, and is, in a more preferred embodiment, part of a vector, in which it may be functionally linked with a promoter that allows for expression, preferably overexpression of the nucleic acid.

In a preferred embodiment, said nucleic acid is inside a cell capable of expressing it to the effect that the inventive polypeptide or a variant thereof is made and, more preferably, routed to the surface of the cell. Said cell comprising the nucleic acid encoding the inventive polypeptide may be used according to the present invention. The cell may be any kind of cell capable of expressing the nucleic acid, for example a prokaryotic or eukaryotic cell. In preferred embodiment, the cell is a eukaryotic cell such as a yeast cell, a eukaryotic cell from a multicellular organism, for example an insect cell, more preferably a mammalian cell, for example a mouse cell, and most preferably a human cell.

The person skilled in the art is familiar with methods used to synthesize, modify and amplify such a nucleic acid and to transfect cells using such a nucleic acid, preferably in a vector that allows for the transient or permanent maintenance or expression of the nucleic acid in the cell. The person skilled in the art is also familiar with a variety of suitable vectors, of which are commercially available, for example from Origene. For example, a vector encoding for fusion constructs with a C-terminal GFP may be used. The cell may be of eukaryotic or prokaryotic origin and is preferably a mammalian cell, for example a HEK293, CHO or COS-7 cell. The cell comprising the nucleic acid encoding for the inventive polypeptide may be a recombinant cell or an isolated cell wherein the term “isolated” means that the cell is enriched such that, compared to the environment of the wild type of said cell, fewer cells of other differentiation or species or in fact no such other cells are present.

The inventive teachings may not only be used for a diagnosis, but also for preventing or treating a disease, more specifically a method for preventing or treating a disease, comprising the steps a) reducing the concentration of autoantibodies binding to the inventive polypeptide in the subject’s blood and/or b) administering one or more immunosuppressive pharmaceutical substances, preferably selected from the group comprising rituximab, prednisone, methylprednisolone, cyclophosphamide, mycophenolatemofetil, intravenous immunoglobulin, tacrolimus, cyclosporine, methotrexate, azathioprine and/or the pharmaceutical composition according to claim 7, wherein the disease is preferably selected from the group comprising cancer, preferably adenocarcinoma, and a neurological disorder characterized by two or more symptoms selected from the group comprising mixed movement disorder, acute decline of visual performance, dysarthria and dysphagia.

The person skilled in the art will appreciate that any of the preferred embodiments discussed throughout this application may be applied to any of the aspects of the inventions.

EXAMPLES

The following examples demonstrate that the neurological disorder disease associated with one or more symptoms selected from the group comprising mixed movement disorder, acute decline of visual performance, dysarthria and dysphagia is related to the emergence of autoantibodies against human neuronal Na(+)/K(+) ATPase. They could be detected in a patient clinically diagnosed as suffering from said disease whilst no such antibodies could be detected in healthy subjects or patients suffering from other neurological diseases.

These autoantibodies bind, as shown herein, specifically to human neuronal Na(+)/K(+) ATPase as well as variants thereof, more specifically mammalian homologues such as those from rat, mouse and pig. These homologues have a sequence identity of approximately 83%.

Characterization of the Patient

The 66-year-old female patient first developed blurred vision and ataxia in November 2012. MRI scan of the brain revealed subcortical white-matter-lesions. Cerebrospinal fluid examination showed a lymphomonocytotic pleocytosis (12 cells/μL), elevated protein levels (104 g/L), and oligoclonal bands. The symptoms improved after intravenous corticosteroid therapy for 3 days. A chronic inflammatory disease of the central nervous system was suspected.

In February 2013 the patient was readmitted with progressive ataxia, she was unable to walk without assistance, ocular movements were saccadic, and vision was reduced to 0.2 on both eyes. Cerebrospinal fluid examination showed a lymphomonocytotic pleocytosis (46 cells/μL) with plasma cells, elevated protein levels (83.6 g/L), and oligoclonal bands. Under consideration of a paraneoplastic syndrome the patient received polyvalent immunoglobulins (2 g/kg i.v. over 5 days). PET-CT revealed a hypermetabolic colorectal tumor. The tumor was completely resected. Histopathological analysis showed an ulcerative adenocarcinoma of low differentiation. Histopathological analysis of the lymph nodes revealed no metastases.

The patient further received immunoglobulins (0.4 g/kg i.v. every 4 weeks) under which the cerebellar symptoms were stable and adjuvant chemotherapy was recommended.

In August 2013 the symptoms again deteriorated. The patient suffered from a severe dysarthria and dysphagia, vertical gaze palsy, severe ataxic limb movements, and spastic tetraparesis. She was unable to leave her bed. Plasmapheresis was performed 6 times without improvement of the alleged paraneoplastic syndrome. PET-CT showed retroperitoneal metastases of the lymph nodes. A CT guided needle biopsy of the lymph nodes was performed which again histologically showed an adenocarcinoma of low differentiation. A palliative chemotherapy due to the standard FOLFIRI regimen was started. The patient deceased in November 2013, an autopsy was not performed.

Initial Serological Work-Up of the Patient

The initial work-up was performed in February 2013. Indirect immunofluorescence assay (IFA) was performed according to the standard incubation protocol for IFA assays provided by EUROIMMUN. Briefly, slides with 4 μm cryosections of mammalian brain tissues were incubated with the patient serum diluted 1:10 to 1:10,000 in PBS, 0.2% Tween-20 (sample buffer) for 30 minutes at 25° C. After thorough washing with sample buffer the slide was incubated with anti-human-IgG conjugated to fluorescein-isothiocyanate (FITC, EUROIMMUN) for 30 minutes at 25° C. After another washing step the slides were inspected with a fluorescence microscope. Rat and primate cerebellum showed strong IgG stainings of both granular and molecular layer, but no staining of Purkinje cells was observed (FIGS. 1A and 1B). A similar intense staining across all layers was obtained with porcine cerebellum whereas a staining of the neuropil was recognized on rat hippocampus (FIGS. 1C and 1D). The incubation of cryosections from murine whole brain and of primate hypophysis, hypothalamus, cerebrum, and medulla spinalis revealed a staining of the neuropil in all parts of the brain without any distinct features. Additionally, cardiac myolemma, intestinal myenteric and submucosal nerves, and gastric parietal cells were stained (FIGS. 1E and 1F).

Further monospecific immunofluorescence (IFA) analyses with HEK293 cells recombinantly expressing known neural autoantigens (Hu, Yo, Ri, CV2, PNMA1, PNMA2, DNER/Tr, MAG, MP0, GAD65, amphiphysin, recoverin, GABA B receptor, glycine receptor, DPPX, aquaporin-4, NMDA receptor, AMPA receptors, LGI1, CASPR2) turned out negative. The analysis of the IgG subclass distribution revealed an exclusive IgG2 reactivity.

A follow-up serum was analyzed in early August 2013 followed by a serum/CSF pair two weeks later. The same reactivity pattern as in the initial serum sample was.

Identification of Brain-Specific Na(+)/K(+) ATPase as the Target Autoantigen

Figure 2:
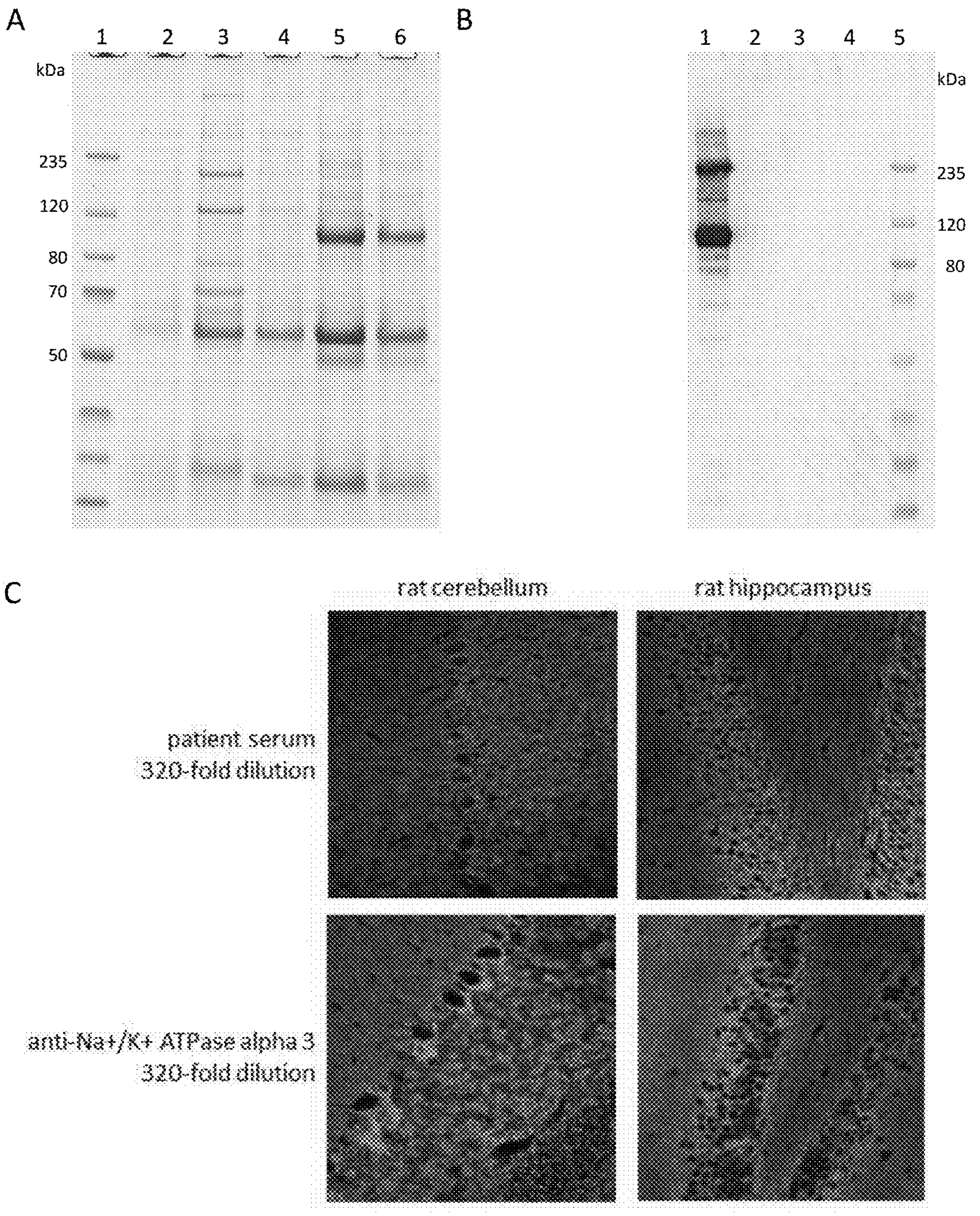
FIG. 2 depicts the results of solid phase-supported immunoprecipitation and verification of the identified antigen. A: SDS-PAGE analysis of eluates of different immunoprecipitations stained with colloidal coomassie. Lane 1: molecular weight marker, lane 2-4: rat cerebellum precipitated with non-healthy control sera, lane 5: rat cerebellum precipitated with patient serum, lane 6: pig cerebellum precipitated with patient serum. B: Western Blot analysis of eluates of different immunoprecipitations, detected by a monoclonal anti-Na+/K+-ATPase alpha 3 antibody (Dianova). Lane 1: rat cerebellum precipitated with patient serum, lanes 2-4: rat cerebellum precipitated with non-healthy control sera, lane 5: molecular weight marker. C: Immunofluorescence staining of rat cerebellum and rat hippocampus with patient serum and anti-Na+/K+ ATPase alpha 3 antibody. Nuclei were counterstained by incubation with TO-PRO-3 iodide.
Figure 3:
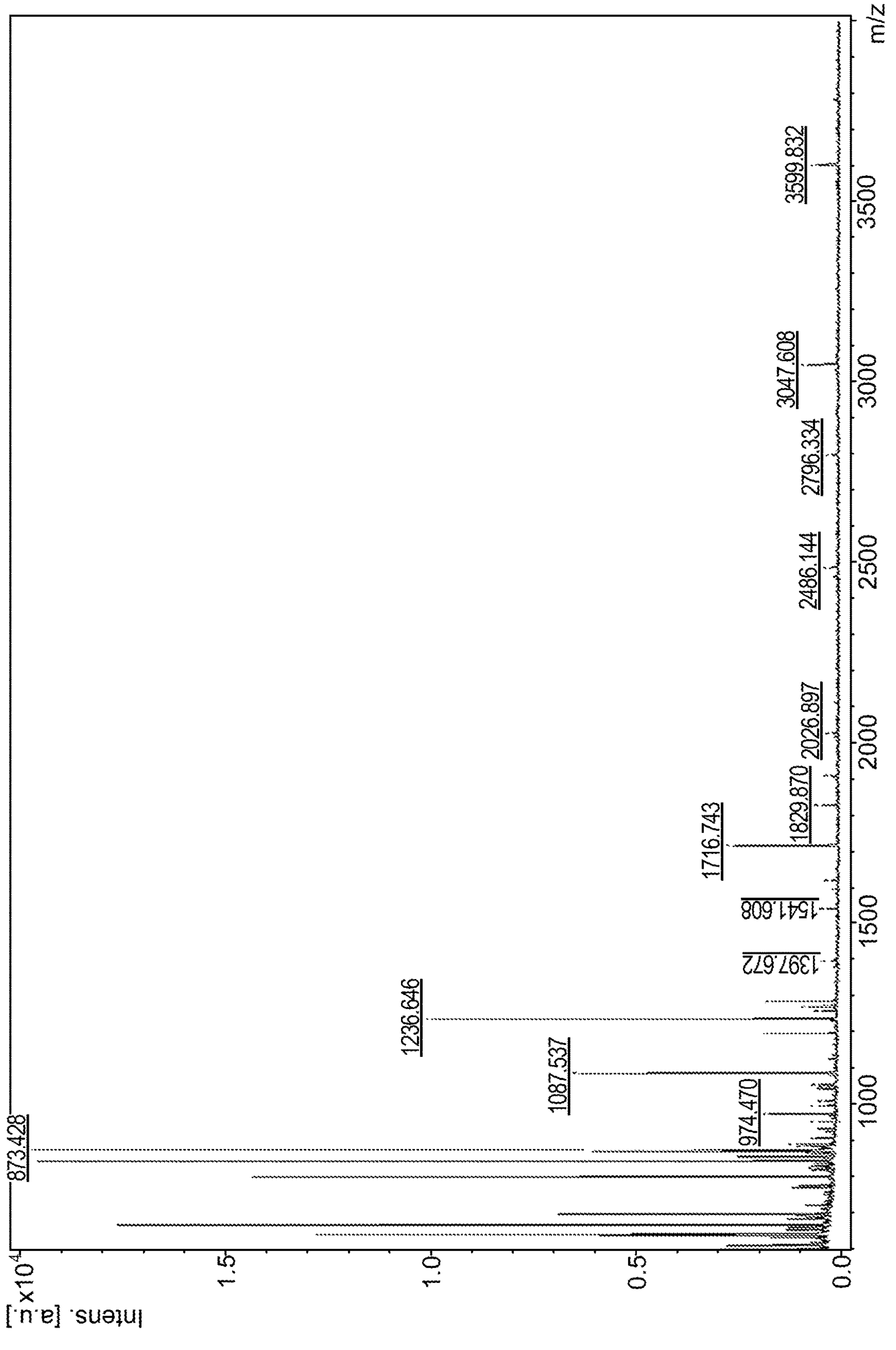
FIG. 3 shows mass spectrometry data relating to the identification of *R. norvegicus* neuronal (Na+/K+) ATPase as the antigen binding to autoantibodies isolated.

Solid phase-supported immunoprecipitation was performed using 1:100 diluted patient serum or sera from healthy controls together with cryosections of rat or pig cerebellum. Immunoprecipitates contained high amounts of IgG when patient serum was used whereas they were generally low after incubation of sera from healthy controls (FIG. 2A). Next to the immunoglobulins the immunoprecipitated patient serum showed protein bands corresponding to molecular masses of approximately 100 kDa and 50 kDa in SDS-PAGE stained with colloidal coomassie (FIG. 2A). These bands were absent in the control samples. The 100 kDa proteins were identified as ATPase, Na+/K+ transporting, alpha 3 polypeptide from *Rattus norvegicus* (UNIPROT acc. #P06687) and *Sus scrofa* (UNIPROT acc. #D2WKD7), respectively. The 50 kDa proteins were identified as the corresponding beta-1 subunit from *Rattus norvegicus* (UNIPROT acc. #P07340). A representative set of mass spectrometry data is shown in FIG. 3. Key data obtained are shown in Table 1.

Western Blot analysis with a monoclonal anti-Na+/K+ ATPase alpha-3 antibody showed a strong reaction at 100 kDa of the immunoprecipitate obtained with the patient serum, while there were no reactions with fractions obtained with three control sera (FIG. 2B). When used in IFA the monoclonal anti-Na+/K+ ATPase alpha-3 antibody produced fluorescence patterns matching those generated by the patient serum (FIG. 2C).

Figure 4A:
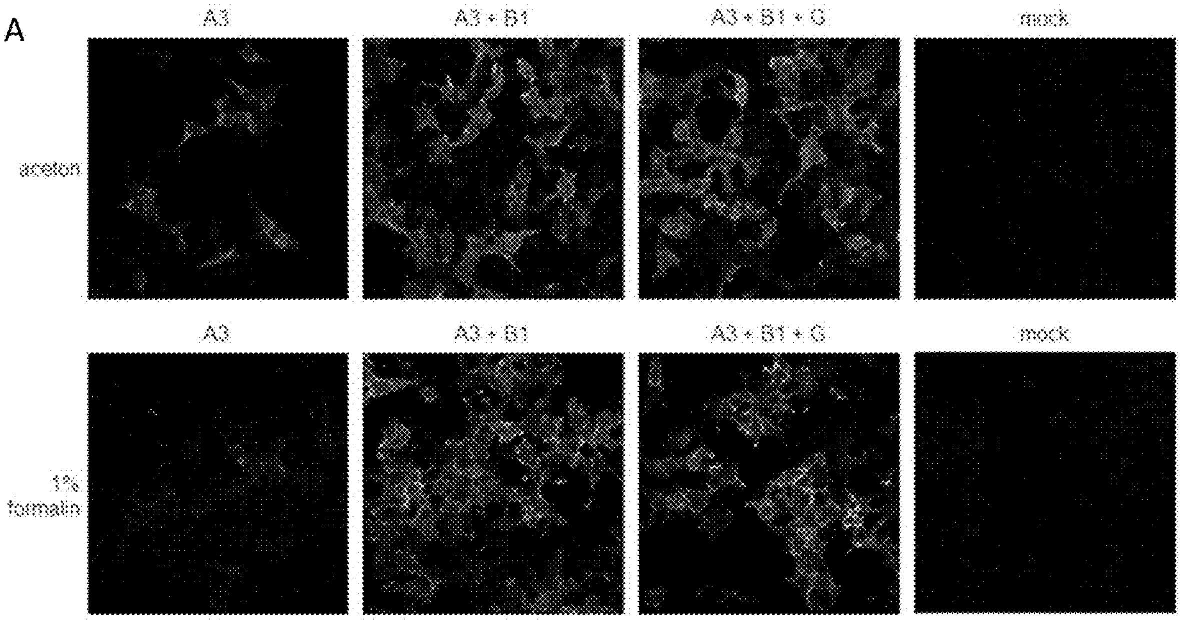
FIGS. 4A and 4B depict the results of immunofluorescence analysis of transfected HEK293 cells.
Figure 4B:
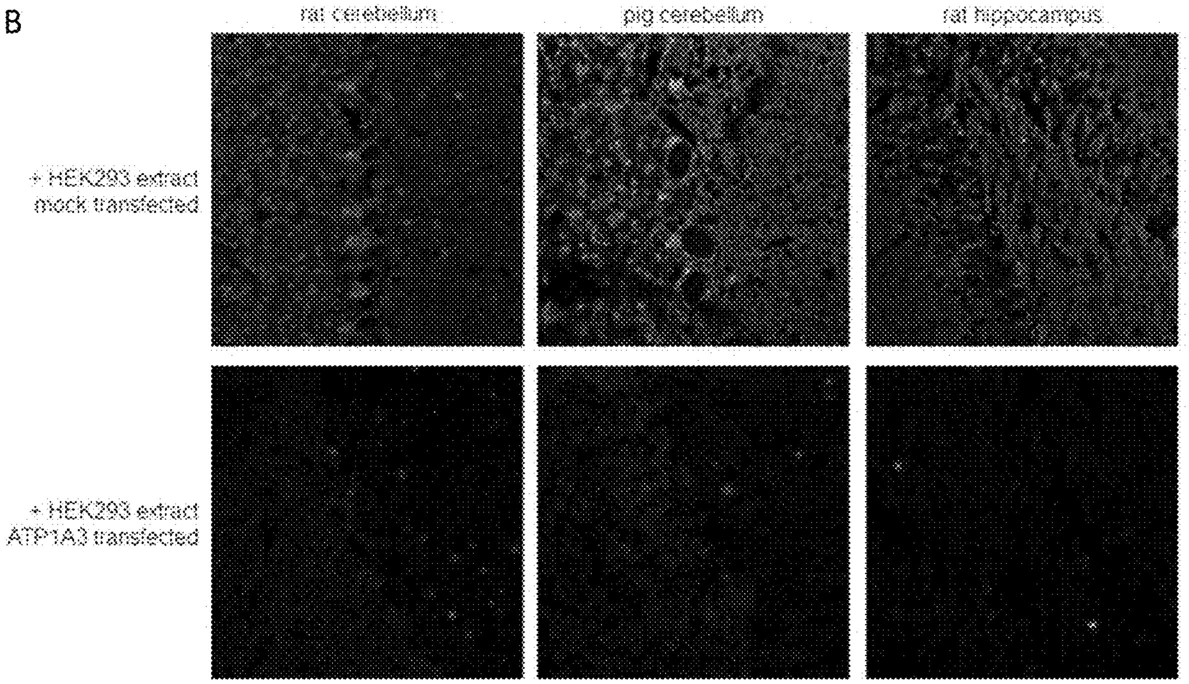

As a proof for the correct antigen identification, all available patient samples were then analyzed by IFA with HEK293 expressing ATP1A3 alone or in conjunction with ATP1B1 and/or ATP1 G and with mock-transfected controls (FIG. 4A). All samples produced characteristic staining patterns on cells expressing ATP1A3 independent of the type of fixation (acetone or 1,825% (w/v) formalin). The fluorescence intensity was highest when all subunits were co-expressed and when formalin fixation was avoided. In contrast, individual expression of ATP1B1 or ATP1 G or mock-transfection did not result in any antibody binding. The congruence of the patient autoantibodies' target and ATP1A3 was further demonstrated by the dose-dependent competitive abolition of antibody binding to brain tissue by HEK293 fractions containing ATP1A3 (FIG. 4B). Antibody binding was unaffected when comparable fractions containing ATP1B1 or ATP1 G individually were used.

In order to analyze the specificity of the ATP1A3 substrate, 34 sera from patients with various neural autoantibodies (anti-NMDAR, anti-Hu, anti-Yo, anti-Ri, anti-AQP4, anti-LGI1, anti-CASPR2) and 50 from healthy blood donors were also analyze by IFA. None of the sera produced a similar immunofluorescence pattern as the index patient's samples on either the recombinant substrate or the different brain tissues.

TABLE 1

A representative set of key data obtained in the mass spec analysis of immunoprecipitation experiments aiming to identify the antigen binding to the autoantibodies isolated.

Sodium/potassium-transporting ATPase subunit alpha-3, *Rattus norvegicus* (UNIPROT acc. # P06687)

MGDKKDDKSS PKKSKAKERR DLDDLKKEVA MTEHKMSVEE VCRKYNTDCV QGLTHSKAQE
ILARDGPNAL TPPPTTPEWV KFCRQLFGGF SILLWIGAIL CFLAYGIQAG TEDDPSGDNL
YLGIVLAAVV IITGCFSYYQ EAKSSKIMES FKNMVPQQAL VIREGEKMQV NAEEVVVGDL
VEIKGGDRVP ADLRIISAHG CKVDNSSLTG ESEPQTRSPD CTHDNPLETR NITFFSTNCV
EGTARGVVVA TGDRTVMGRI ATLASGLEVG KTPIAIEIEH FIQLITGVAV FLGVSFFILS
LILGYTWLEA VIFLIGIIVA NVPEGLLATV TVCLTLTAKR MARKNCLVKN LEAVETLGST
STICSDKTGT LTQNRMTVAH MWFDNQIHEA DTTEDQSGTS FDKSSHTWVA LSHIAGLCNR
AVFKGGQDNI PVLKRDVAGD ASESALLKCI ELSSGSVKLM RERNKKVAEI PFNSTNKYQL
SIHETEDPND NRYLLVMKGA PERILDRCAT ILLQGKEQPL DEEMKEAFQN AYLELGGLGE
RVLGFCHYYL PEEQFPKGFA FDCDDVNFTT DNLCFVGLMS MIDPPRAAVP DAVGKCRSAG
IKVIMVTGDH PITAKAIAKG VGIISEGNET VEDIAARLNI PVSQVNPRDA KACVIHGTDL
KDFTSEQIDE ILQNHTEIVF ARTSPQQKLI IVEGCQRQGA IVAVTGDGVN DSPALKKADI
GVAMGIAGSD VSKQAADMIL LDDNFASIVT GVEEGRLIFD NLKKSIAYTL TSNIPEITPF
LLFIMANIPL PLGTITILCI DLGTDMVPAI SLAYEAAESD IMKRQPRNPR TDKLVNERLI
SMAYGQIGMI QALGGFFSYF VILAENGFLP GNLVGIRLNW DDRTVNDLED SYGQQWTYEQ
RKVVEFTCHT AFFVSIVVVQ WADLIICKTR RNSVFQQGMK NKILIFGLFE ETALAAFLSY
CPGMDVALRM YPLKPSWWFC AFPYSFLIFV YDEIRKLILR RNPGGWVEKE TYY (SEQ ID NO: 14)

| # of peptides identified | Sequence coverage | Score for PMF (Cut-Off: 74) | # of peptides chosen for sequence confirmation | Peptide sequences |
|---|---|---|---|---|
| 23 | 25% | 219 | 2 | LIIVEGCQR (SEQ ID NO: 1); LNIPVSQVNPR (SEQ ID NO: 2) |

Sodium/potassium-transporting ATPase subunit alpha-3, *Sus scrofa* (UNIPROT acc. # D2WKD7)

MGDKKDDKGS PKKGKGTKDR RDLDDLKKEV AMTEHKMSVE EVCRKYNTDC VQGLTHSKAQ
EILARDGPNA LTPPPTTPEW VKFCRQLFGG FSILLWIGAI LCFLAYGIQA GTEDDPSGDN
LYLGIVLAAV VIITGCFSYY QEAKSSKIME SFKNMVPQQA LVIREGEKMQ VNAEEVVVGD
LVEIKGGDRV PADLRIISAH GCKVDNSSLT GESEPQTRSP DCTHDNPLET RNITFFSTNC
VEGTARGVVV ATGDRTVMGR IATLASGLEV GKTPIAIEIE HFIQLITGVA VFLGVSFFIL
SLILGYTWLE AVIFLIGIIV ANVPEGLLAT VTVCLTLTAK RMARKNCLVK NLEAVETLGS

TABLE 1-continued

A representative set of key data obtained in the mass spec analysis of immunoprecipitation experiments aiming to identify the antigen binding to the autoantibodies isolated.

TSTICSDKTG TLTQNRMTVA HMWFDNQIHE ADTTEDQSGT SFDKSSHTWV ALSHIAGLCN
RAVFKGGQDN IPVLKRDVAG DASESALLKC IELSSGSVKL MRERNKKVAE IPFNSTNKYQ
LSIHETEDPN DNRYLLVMKG APERILDRCS TILLQGKEQP LDEEMKEAFQ NAYLELGGLG
ERVLGFCHYY LPEEQFPKGF AFDCDDVNFT TDNLCFVGLM SMIDPPRAAV PDAVGKCRSA
GIKVIMVTGD HPITAKAIAK GVGIISEGNE TVEDIAARLN IPVSQVNPRD AKACVIHGTD
LKDFTSEQID EILQNHTEIV FARTSPQQKL IIVEGCQRQG AIVAVTGDGV NDSPALKKAD
IGVAMGIAGS DVSKQAADMI LLDDNFASIV TGVEEGRLIF DNLKKSIAYT LTSNIPEITP
FLLFIMANIP LPLGTITILC IDLGTDMVPA ISLAYEAAES DIMKRQPRNP RTDKLVNERL
ISMAYGQIGM IQALGGFFSY FVILAENGFL PSNLVGIRLN WDDRTVNDLE DSYGQQWTYE
QRKVVEFTCH TAFFVSIVVV QWADLIICKT RRNSVFQQGM KNKILIFGLF RRNPGGWVEK ETYY
(SEQ ID NO: 15)

| # of peptides identified | Sequence coverage | Score for PMF (Cut-Off: 74) | # of peptides chosen for sequence confirmation | Peptide sequences |
|---|---|---|---|---|
| 16 | 18% | 166 | 2 | LIIVEGCQR (SEQ ID NO: 1); LNIPVSQVNPR (SEQ ID NO: 2) |

Detection of ATP1A3 in Tumor Tissue

Figure 5:
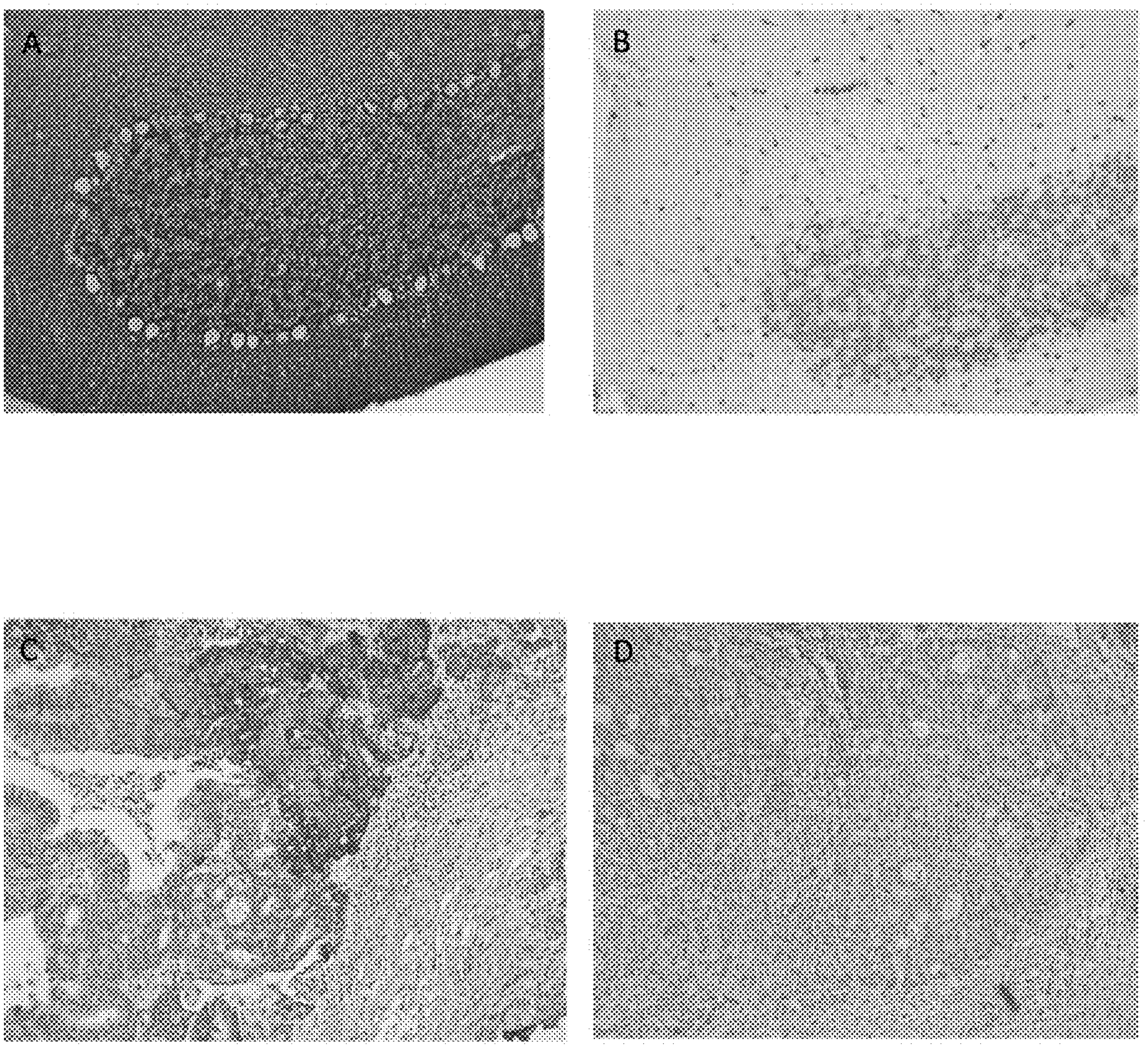
FIG. 5 shows the results of immunohistochemical staining of mouse brain and tumour tissue. A: anti-Na+/K+ ATPase alpha 3, 500-fold diluted, on mouse cerebellum. B: universal negative control on mouse cerebellum. C: anti-Na+/K+ ATPase alpha 3, 1000-fold diluted, on patient colon carcinoma. D: universal negative control on patient colon carcinoma.

The validity of using the murine monoclonal antibody for the detection of ATP1A3 in formalin-fixed, paraffin-embedded and heat-retrieved tissue sections was demonstrated by the staining of murine brain (FIG. 5A). The incubation of the patient's colorectal adenocarcinoma tissue produced staining of cell-clusters characteristic for tumor tissues whereas the surrounding healthy tissue was void of any staining (FIG. 5C). Consistently, colon tissue from healthy donors was also not stained.

The invention claimed is:

1. A kit comprising:

(1) a carrier, (2) a cell recombinantly expressing a first polypeptide comprising the alpha 3 subunit of the human neuronal Na(+)/K(+) ATPase, wherein the cell is immobilized on the carrier and is not lysed, and (3) a labeled anti-human-IgG antibody.

2. The kit of claim 1, wherein the carrier is a nitrocellulose membrane.

3. The kit of claim 1, wherein the carrier is a glass plate or slide, biochip, microtiter plate, bead, chromatograph column, or membrane.

4. The kit of claim 1, further comprising a second polypeptide, wherein the second polypeptide is different from the first polypeptide, and is immobilized on the carrier.

5. The kit of claim 4, wherein the second polypeptide is a negative or positive control for binding between the first polypeptide and an autoantibody against the alpha 3 subunit of human neuronal Na(+)/K(+) ATPase.

6. The kit of claim 1, wherein the first polypeptide is a fusion protein.

* * * * *